(12) United States Patent
Zhu et al.

(10) Patent No.: US 9,723,841 B2
(45) Date of Patent: Aug. 8, 2017

(54) HERBICIDAL FORMULATIONS COMPRISING GLYPHOSATE AND ALKOXYLATED GLYCERIDES

(75) Inventors: Shawn Zhu, Stormville, NY (US); Norman R. Pallas, St. Louis, MO (US)

(73) Assignee: AKZO NOBEL N.V., Arnhem (NL)

( * ) Notice: Subject to any disclaimer, the term of this patent is extended or adjusted under 35 U.S.C. 154(b) by 1128 days.

(21) Appl. No.: 13/255,363

(22) PCT Filed: Mar. 11, 2010

(86) PCT No.: PCT/US2010/026970
§ 371 (c)(1),
(2), (4) Date: Oct. 25, 2011

(87) PCT Pub. No.: WO2010/105047
PCT Pub. Date: Sep. 16, 2010

(65) Prior Publication Data
US 2012/0040830 A1 Feb. 16, 2012

Related U.S. Application Data

(60) Provisional application No. 61/209,834, filed on Mar. 11, 2009.

(51) Int. Cl.
*A01N 57/20* (2006.01)
*A01P 13/00* (2006.01)
*A01N 25/30* (2006.01)

(52) U.S. Cl.
CPC ............ *A01N 57/20* (2013.01); *A01N 25/30* (2013.01)

(58) Field of Classification Search
CPC ............................... A01N 25/30; A01N 57/20
See application file for complete search history.

(56) References Cited

U.S. PATENT DOCUMENTS

| | | |
|---|---|---|
| 1,505,560 A | 8/1924 | Grun |
| 2,197,339 A | 4/1940 | Gooding et al. |
| 2,197,340 A | 4/1940 | Gooding et al. |
| 2,206,167 A | 7/1940 | Edeler et al. |
| 2,206,168 A | 7/1940 | Edeler et al. |
| 2,383,581 A | 8/1945 | Arrowsmith et al. |
| 2,474,740 A | 6/1949 | Ittner |
| 2,496,328 A | 2/1950 | Bell et al. |
| 2,634,278 A | 4/1953 | Kuhrt |
| 2,634,279 A | 4/1953 | Kuhrt |
| 2,748,354 A | 5/1956 | Lavoo |
| 2,875,221 A | 2/1959 | Birnbaum |
| 2,909,540 A | 10/1959 | Woods |
| 3,079,412 A | 2/1963 | Chang et al. |
| 3,083,216 A | 3/1963 | Alsop et al. |
| 3,095,431 A | 6/1963 | Giddings et al. |
| 3,102,129 A | 8/1963 | Birnbaum et al. |
| 3,305,377 A | 2/1967 | Mahomed |
| 3,313,834 A | 4/1967 | Allen et al. |
| 4,025,540 A | 5/1977 | Kleemann et al. |
| 4,681,900 A | 7/1987 | Iwasaki |
| 4,754,075 A | 6/1988 | Knopf et al. |
| 4,950,441 A | 8/1990 | Beseda et al. |
| 5,114,900 A | 5/1992 | King |
| 5,120,697 A | 6/1992 | King |
| 5,747,305 A | 5/1998 | Jackson |
| 5,750,468 A | 5/1998 | Wright et al. |
| 6,028,046 A | 2/2000 | Arif |
| 6,566,305 B1 | 5/2003 | Milius et al. |
| 6,723,863 B2 | 4/2004 | Lee et al. |
| 6,737,381 B1 | 5/2004 | Milius et al. |
| 6,762,289 B1 | 7/2004 | O'Lenick, Jr. et al. |
| 6,861,068 B2 | 3/2005 | Ng et al. |
| 2002/0160918 A1 | 10/2002 | Lewis et al. |
| 2004/0071653 A1* | 4/2004 | Bratescu et al. ........... 424/70.24 |
| 2004/0224850 A1 | 11/2004 | Lindner |
| 2005/0261130 A1* | 11/2005 | Lennon et al. ............... 504/206 |
| 2006/0154824 A1* | 7/2006 | Yoshii ................... A01N 47/36 504/211 |
| 2007/0129254 A1 | 6/2007 | Lindner |
| 2008/0299228 A1 | 12/2008 | Harris et al. |
| 2009/0017074 A1 | 1/2009 | Maitre-Wilmotte et al. |
| 2009/0081142 A1 | 3/2009 | Omura et al. |
| 2009/0170704 A1 | 7/2009 | Kober et al. |
| 2009/0258806 A1 | 10/2009 | Hoffmann et al. |
| 2009/0286699 A1 | 11/2009 | Saini et al. |

FOREIGN PATENT DOCUMENTS

| | | |
|---|---|---|
| EP | 1045021 A1 | 10/2000 |
| WO | 02/43493 A1 | 6/2002 |
| WO | 2006034426 A1 | 3/2006 |
| WO | 2006034459 A1 | 3/2006 |
| WO | 2007109791 A2 | 9/2007 |

OTHER PUBLICATIONS

International Search Report, PCT/US2010/026970, dated Feb. 17, 2011, 4 pages.
Anderson et al., "Alkoxylated Glyceride Emulsifiers in Agriculture Applications", ASTM International, 2001, pp. 136-144.
Hama et al., "Preparation and Properties of Ethoxylated Fatty Methyl Ester Nonionics", Journal of the American Oil Chemists' Society, vol. 72, No. 7, p. 781, 1985.
"Low Irritation Additives for Personal Care", Witco Corporation, 1998, 5 pages.
Sonntag, Norman O. V., "Glycerolysis of Fats and Methyl Esters—Status, Review, and Critique," JAOCS, vol. 59, No. 10 (Oct. 1982), pp. 795A-802A.
Evonik Industries, TEGOSOFT(R) GC, TEGOSOFT(R) GMC 6 product information, 2008, 4 pages.
Evonik Industries, REWODERM(R) LI 67-75 product information, 2008, 3 pages.
Evonik Industries, REWODERM(R) LI 520-70 product information, 2008, 3 pages.
Evonik Industries, REWODERM(R) LI 63 product information, 2008, 3 pages.
Evonik Industries, REWODERM(R) LI S 80 product information, 2008, 4 pages.

* cited by examiner

*Primary Examiner* — Ali Soroush
*Assistant Examiner* — Genevieve S Alley
(74) *Attorney, Agent, or Firm* — McDonnell Boehnen Hulbert & Berghoff LLP

(57) ABSTRACT

The present invention generally relates to herbicidal compositions, and more particularly, herbicidal compositions containing glyphosate or a salt thereof and a surfactant comprising at least one mono and/or diglyceride alkoxylate.

32 Claims, 2 Drawing Sheets

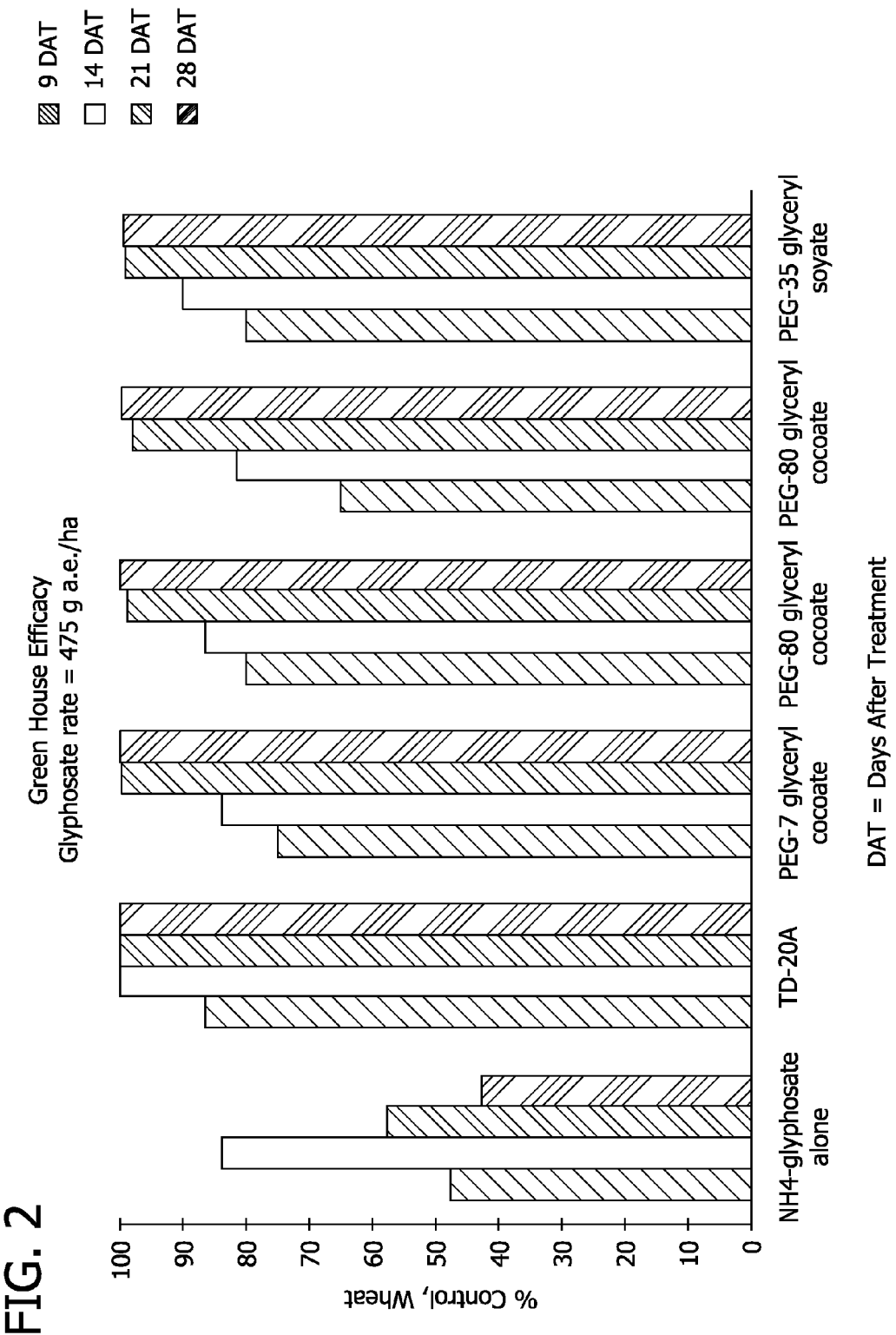

HERBICIDAL FORMULATIONS COMPRISING GLYPHOSATE AND ALKOXYLATED GLYCERIDES

REFERENCE TO RELATED APPLICATIONS

This application is the U.S. national stage application of International Patent Application No. PCT/US2010/026970, filed Mar. 11, 2010, which claims the benefit of U.S. Provisional Application No. 61/209,834, filed Mar. 11, 2009, the entire disclosures of which are incorporated herein by reference.

FIELD OF THE INVENTION

The present invention generally relates to herbicidal compositions, and more particularly, herbicidal compositions containing glyphosate or a salt thereof and a surfactant comprising at least one mono and/or diglyceride alkoxylate.

BACKGROUND OF THE INVENTION

N-phosphonomethylglycine, otherwise known as glyphosate, is well known in the art as an effective post-emergent foliar applied herbicide. Glyphosate is an organic compound with three acidic groups and in its acid form is relatively insoluble in water. Glyphosate is, therefore, normally formulated and applied as a water-soluble salt. Although monobasic, dibasic and tribasic salts of glyphosate can be made, it has generally been preferred to formulate and apply glyphosate, in the form of a monobasic salt, for example as a mono-(organic ammonium) salt such as the mono (isopropylamine), often abbreviated to IPA salt.

The present application refers to and is applicable to all glyphosate salts including, but not limited to, "ammonium", "monoammonium" and "diammonium" salts of glyphosate. For example, the glyphosate salts useful in the present context include, but are not limited to salts of isopropylamine, monoethanolamine, diethanolamine, potassium, ammonium, trimesium, or mixtures thereof. Glyphosate rates and concentrations given herein, even where the glyphosate is present as a salt or salts, are expressed as acid equivalent (a.e.) unless the context demands otherwise.

Glyphosate salts generally require the presence of a suitable surfactant to improve bioefficacy and enhance overall herbicidal performance. The surfactant may be provided in the concentrate formulation, or it may be added by the end user to the diluted spray solution. The choice of surfactant is very important since there are wide variations among surfactants in their ability to enhance the herbicidal efficacy of glyphosate.

The herbicidal efficacy of glyphosate salt solutions is highly dependent upon two factors: selecting a suitable surfactant and providing an effective (as high a concentration as possible) amount of that surfactant in the concentrate formulation. Glyphosate itself is mild to the eyes, has low aquatic toxicity and is readily biodegradable. Alkylamine based surfactants have been used and have provided excellent bioefficacy enhancing ability to glyphosate. These surfactants may under certain conditions exhibit higher eye irritation potential than various other surfactants, but are nonetheless suitable and safe for use. However, alternatives to alkylamine based surfactants having lower eye irritation properties and lower toxicity to aquatic life would be advantageous in certain circumstances.

It is known to those skilled in the art that finding a suitable surfactant with good efficacy enhancing property for glyphosate is difficult. However, finding a suitable surfactant with low eye irritation and aquatic toxicity properties in addition to good efficacy enhancing property is more difficult. Very few known surfactants (e.g., alkyl polyglycoside, short chain phosphate ester, alkylamine oxide and alkyl betaine) with good eye irritation and aquatic toxicity properties have been used in glyphosate formulations. However, these surfactants are not very efficacious for glyphosate.

Accordingly, it is desirable to develop a suitable surfactant with low eye irritation and aquatic toxicity properties in addition to good efficacy enhancing property for glyphosate. These and other objectives are met by the surfactants and herbicidal formulations of the present invention.

SUMMARY OF THE INVENTION

The present invention generally relates to herbicidal formulations comprising alkoxylated mono and/or diglycerides. Advantageously, mono and diglyceride alkoxylates (e.g., ethoxylates) are common ingredients found in, for example, tear-free baby shampoos, and accordingly have very low irritation to eyes and low toxicity to aquatic life. Mono and diglyceride alkoxylates utilized in accordance with the present invention include those represented by the following formulae.

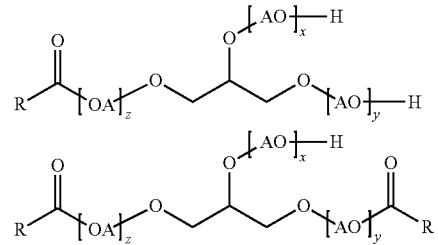

wherein each R group is independently selected from $C_8$-$C_{22}$ linear or branched, saturated or unsaturated aliphatic group, each A group is the same or different and is selected from $C_1$ to $C_4$ linear or branched alkyl groups, each of x, y and z can be from 0 to 100, with the proviso that x+y+z is from 5 to 200. In another embodiment, each R group is $C_{12}$-$C_{18}$ linear or branched, saturated or unsaturated aliphatic group and each A group is ethylene. In a further embodiment, R is a group of the formula:

$$R^{10}-[OA^1]v-R^{11},$$

where
(i) $R^{10}$ is bonded to the carbon of the acyl group (ii) each $R^{10}$ is selected from a $C_8$-$C_{22}$ linear or branched, saturated or unsaturated aliphatic group (iii) each $A^1$ is the same or different and is selected from $C_1$ to $C_4$ linear or branched alkyl groups, with v from 1 to 100 and (iv) each $R^{11}$ is selected from hydrogen and a $C_8$-$C_{22}$ linear or branched, saturated or unsaturated aliphatic group.

A preferred alkoxylated glyceride is ethoxylated glyceride. In another embodiment, the ethoxylated glyceride has a mono to di ratio of greater than about 50:50, preferably in the range of 60:40 to 99:1. Various glyphosate formulations generally have a weight ratio of glyphosate (a.e.) to the alkoxylated mono and diglycerides of from about 20:1 to about 2:1, or from about 10:1 to about 3:1.

The present invention is further directed to herbicidal formulations comprising alkoxylated mono and diglycerides corresponding to the following formulae:

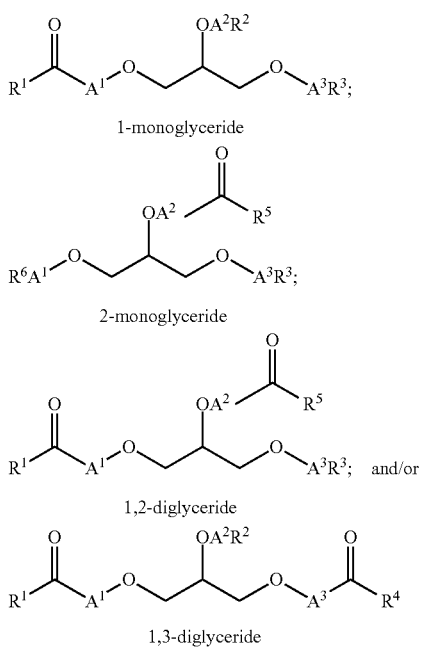

1-monoglyceride 2-monoglyceride 1,2-diglyceride 1,3-diglyceride wherein each of $R^1$, $R^4$ and $R^5$ is independently selected from $C_8$ to $C_{22}$ linear or branched, saturated or unsaturated aliphatic groups, each of $R^2$, $R^3$, and $R^6$ is independently selected from H and a lower alkyl, lower alkenyl, or aryl group, and each of $A^1$, $A^2$ and $A^3$ is independently either a carbon to oxygen bond or an alkylene oxide group oriented to have a terminal O bonded to a C and a terminal C bonded to an O and containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, provided that each of the alkoxylated mono and diglycerides contains between 5 and 200 alkylene oxide units. In one embodiment, $R^1$, $R^4$, and/or $R^5$ is each independently a group of the formula

where
(i) $R^{10}$ is bonded to the carbon of the acyl group (ii) each $R^{10}$ is selected from a $C_8$-$C_{22}$ linear or branched, saturated or unsaturated aliphatic group (iii) each A is the same or different and is selected from $C_1$ to $C_4$ linear or branched alkyl groups, with w from 1 to 100 and (iv) each $R^{11}$ is selected from hydrogen and a $C_8$-$C_{22}$ linear or branched, saturated or unsaturated aliphatic group.

In accordance with various preferred embodiments of the present invention, the formulation is characterized by one or more of the following:
 (i) a mixture of ethoxylated mono- and diglycerides having a mono to di ratio of greater than about 50:50 (wt. ratio); and/or
 (ii) a glyphosate content of at least about 180 g a.e./l; and/or
 (iii) a weight ratio of glyphosate (a.e.) to the sum of alkoxylated mono and diglyceride surfactant of between about 1:1 and about 30:1; and/or
 (iv) a concentration of glyphosate in the range of from about 360 to about 600 g a.e./l, and the weight ratio of glyphosate (wt % a.e.) to the alkoxylated glyceride surfactant is between about 2:1 and about 25:1.

In various other preferred embodiments, the herbicidal formulations of the present invention comprise at least one herbicidally active compound, provided the herbicidally active compound is not a sulfonylurea compound.

BRIEF DESCRIPTION OF THE DRAWINGS

FIG. 2 provides greenhouse testing data collected as set forth in Example 2.

DETAILED DESCRIPTION OF THE PREFERRED EMBODIMENTS

Figure 1:
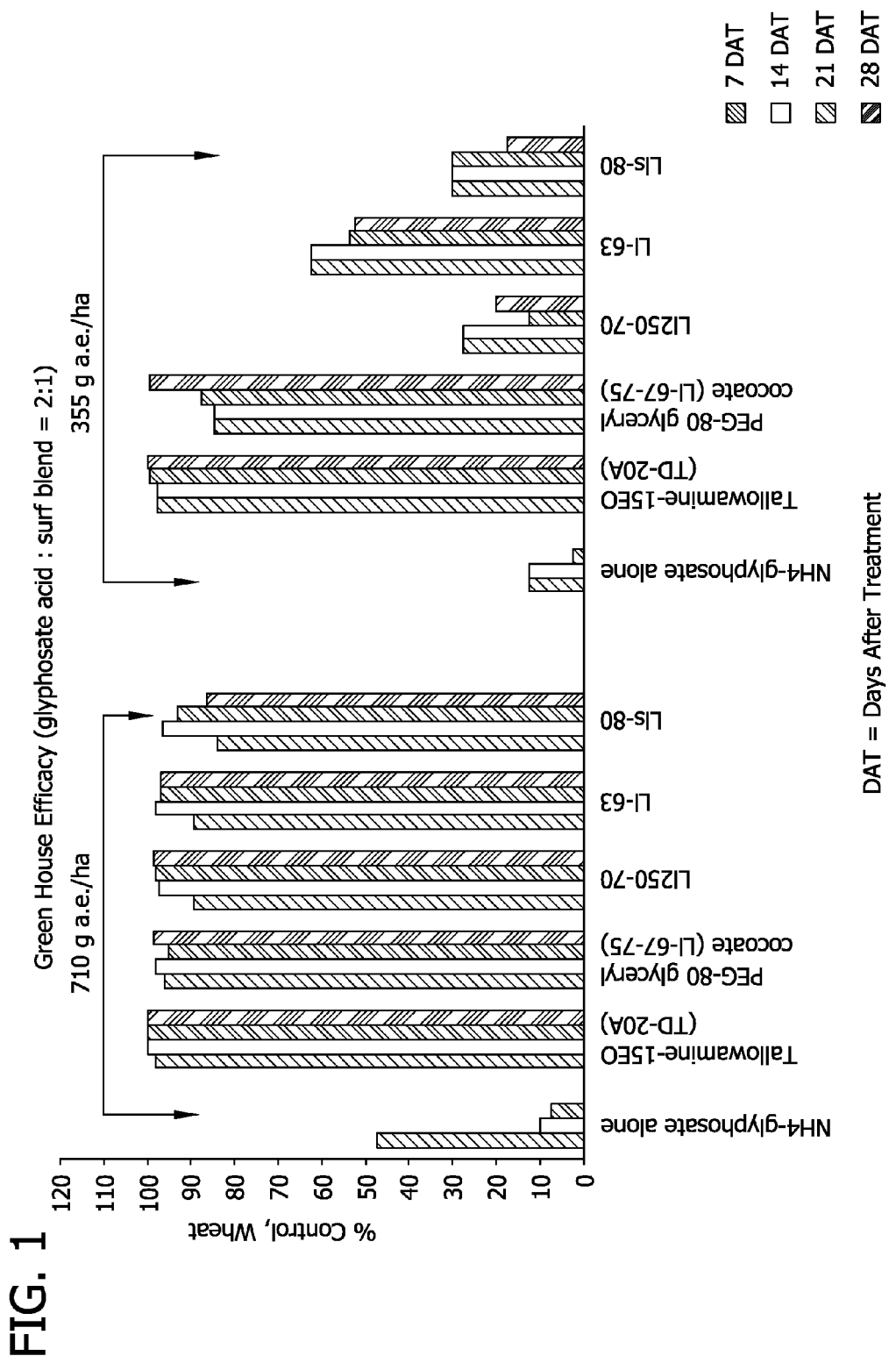
FIG. 1 provides greenhouse testing data collected as set forth in Example 1.

The present invention generally relates to herbicidal formulations comprising alkoxylated mono and/or diglycerides and at least one herbicidally active compound.

In various preferred embodiments, the herbicidally active compound employed in the formulations of the invention preferably comprises glyphosate. Glyphosate is an organic compound that at neutral pH contains three acidic protonable groups, and in its acid form is relatively insoluble in water. Therefore, glyphosate is normally formulated and applied as a water-soluble salt. Although monobasic, dibasic, and tribasic salts of glyphosate can be made, it has generally been preferred to formulate and apply glyphosate in the form of a monobasic salt, for example as a mono- (organic ammonium) salt such as the mono (isopropylamine), often referred to as IPA, salt, or as either monobasic or dibasic ammonium (NH$_4$) salt. Other suitable glyphosate salts include sodium (Na), potassium (K), monoethanolamine (MEA), diethanolamine (DEA), triethanolamine (TEA), trimesium (TMS), and mixtures thereof. Generally, the glyphosate concentration of a suitable application mixture is from about 0.5 to 2.0 wt % a.e., or from about 0.5 to about 1.0 wt %. a.e. In various embodiments, the glyphosate salt is selected from the group consisting of sodium, potassium, ammonium, isopropylamine, monethanolamine, diethanolamine, triethanolamine, trimesium salts, and mixtures thereof. In various other embodiments, the glyphosate salt is selected from the group consisting of ammonium glyphosate, diammonium glyphosate, sodium glyphosate, potassium glyphosate, isopropylammonium glyphosate, and the monethanolamine salt of glyphosate. Typically, the formulations of the present invention have a pH greater than about 4, greater than about 4.6, greater than about 4.7, greater than about 4.8, or greater than about 4.9.

I. Alkoxylated Glycerides

The surfactants of the present invention comprise alkoxylated mono and/or diglycerides, and have demonstrated the ability to enhance the bioefficacy of glyphosate formulations while at the same time having very low irritation to eyes and low toxicity to aquatic life. The mono and diglyceride alkoxylates of the invention include, but are not limited to the following classes of compounds:

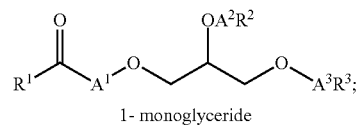

1- monoglyceride

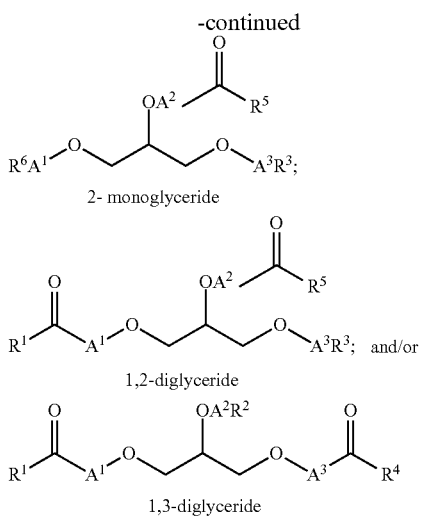

2-monoglyceride 1,2-diglyceride and/or 1,3-diglyceride wherein each of $R^1$, $R^4$ and $R^5$ is independently selected from $C_8$ to $C_{22}$ linear or branched, saturated or unsaturated aliphatic groups, each of $R^2$, $R^3$, and $R^6$ is independently selected from H and a lower alkyl, lower alkenyl, or aryl group, and each of $A^1$, $A^2$ and $A^3$ is independently either a carbon to oxygen bond or an alkylene oxide group containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, provided that each of the alkoxylated mono and diglycerides contains a total of between 5 and 200 alkylene oxide units.

In various preferred embodiments, each of $A^1$, $A^2$, and $A^3$ is independently an alkylene oxide group containing from 1 to 100 alkylene oxide units, from 1 to 50 alkylene oxide units, from 1 to 10 alkylene oxide units, or from 2 to 10 alkylene oxide units.

In various embodiments, each of $A^1$, $A^2$, and $A^3$ is independently an alkylene oxide group including alkylene oxide units independently selected from the group consisting of —[OCH$_2$]—, —[OC$_2$H$_4$]—, —[OC$_3$H$_6$]— and —[OC$_4$H$_8$]—. In various preferred embodiments, each of $A^1$, $A^2$, and $A^3$ is independently an alkylene oxide group including alkylene oxide units independently selected from the group consisting of —[OC$_2$H$_4$]—, —[OC$_3$H$_6$]— and —[OC$_4$H$_8$]—. In various preferred embodiments, each of $A^1$, $A^2$, and $A^3$ generally are independently alkylene oxide groups containing from 1 to 100 alkylene oxide units, typically from 1 to 50 alkylene oxide units, and more typically from 1 to 10 alkylene oxide units (e.g., from 2 to 10). In various other preferred embodiments, $A^1$, $A^2$ and $A^3$ are each alkylene oxide groups containing —[OC$_2$H$_4$]-ethylene oxide units.

$R^1$, $R^2$, $R^3$, $R^4$, $R^5$, and $R^6$ may be derived from a variety of sources that provide alkyl groups including, for example, butyric acid, valeric acid, caprylic acid, capric acid, coco (mainly comprising lauric acid), myristic acid (e.g., from palm oil), soy (mainly comprising linoleic acid, oleic acid, and palmitic acid), or tallow (comprising mainly palmitic acid, oleic acid, and stearic acid).

In accordance with various preferred embodiments, $R^1$, $R^2$, $R^3$, $R^4$, $R^5$, and $R^6$ are each independently derived from soybean oil, palm oil, rapseseed oil, corn oil, or coconut oil.

In various embodiments, $R^1$, $R^4$, and/or $R^5$ is each independently a group of the formula $$R^{10}\text{—[OA]}w\text{-}R^{11},$$

where
(i) $R^{10}$ is bonded to the carbon of the acyl group; (ii) each $R^{10}$ is selected from a $C_8$-$C_{22}$ linear or branched, saturated or unsaturated aliphatic group; (iii) each A is the same or different and is selected from $C_1$ to $C_4$ linear or branched alkyl groups, with w from 1 to 100; and (iv) each $R^{11}$ is selected from hydrogen and a $C_8$-$C_{22}$ linear or branched, saturated or unsaturated aliphatic group. Further in accordance with such embodiments, w is generally from 1 to 75, from 1 to 50, from 1 to 30, or from 1 to 15. $R^{10}$ and $R^{11}$ may be derived from those sources that provide alkyl groups listed above regarding $R^1$, $R^2$, $R^3$, etc. including, for example, soybean oil, palm oil, rapeseed oil, corn oil, and coconut oil.

In various preferred embodiments, the alkoxylated glycerides are mono and diglycerides that correspond to the formulae:

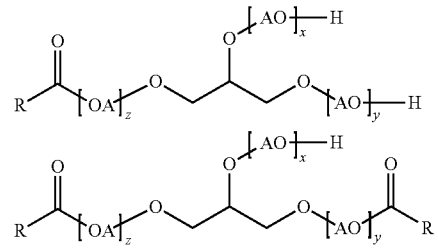

wherein each R group is independently selected from $C_8$-$C_{22}$ linear or branched, saturated or unsaturated aliphatic group, each A group is the same or different and is selected from $C_1$ to $C_4$ linear or branched alkyl groups, each of x, y and z can be from 0 to 100, with the proviso that x+y+z is from 5 to 200. In various embodiments, each R group is $C_{12}$-$C_{18}$ linear or branched, saturated or unsaturated aliphatic group and each A group is ethylene. A preferred alkoxylated glyceride is ethoxylated glyceride.

In accordance with various embodiments, x+y+z=5 to 175, more typically from about 5 to 100, still more typically from about 5 to 50 and, even more typically, from about 5 to 30. In accordance with various embodiments, one or more A groups of Formula I and/or Formula II is a $C_2$ ethyl group. In various preferred embodiments, each A group of Formula I and/or Formula II is a $C_2$ ethyl group. In various embodiments, each R group is independently selected from $C_{12}$-$C_{18}$ linear or branched, saturated or unsaturated alkyl group and each A group is ethylene. R groups may suitably be derived from one or more of the sources set forth above regarding $R^1$, $R^2$, $R^3$, etc. In accordance with these and other preferred embodiments, each R group is independently derived from soybean oil, palm oil, or coconut oil.

In various embodiments, R is a group of the formula $$R^{10}\text{—[OA}^1\text{]}v\text{-}R^{11},$$

where
(i) $R^{10}$ is bonded to the carbon of the acyl group; (ii) each $R^{10}$ is selected from a $C_8$-$C_{22}$ linear or branched, saturated or unsaturated aliphatic group; (iii) each $A^1$ is the same or different and is selected from $C_1$ to $C_4$ linear or branched alkyl groups, with v from 1 to 100; and (iv) each $R^{11}$ is selected from hydrogen and a $C_8$-$C_{22}$ linear or branched, saturated or unsaturated aliphatic group. In accordance with such embodiments v is generally from 1 to 75, from 1 to 50, from 1 to 30, or from 1 to 15. In accordance with various embodiments, $R^{10}$ and/or $R^{11}$ are $C_{12}$-$C_{18}$ linear or branched, saturated or unsaturated alkyl groups. Further in accordance with these and other embodiments, $R^{10}$ and/or $R^{11}$ are independently derived from soybean oil, palm oil, or coconut oil. In various preferred embodiments, $A^1$ is ethylene.

In various preferred embodiments, the surfactant of the present invention comprises an ethoxylated mono- and/or diglyceride. In certain embodiments, the ethoxylated glyceride comprises a mixture of alkoxylated glycerides and, in various preferred embodiments, ethoxylated mono- and diglycerides having a monoglyceride to diglyceride weight ratio of greater than about 50:50, preferably in the range of 60:40 to 99:1, or from 60:40 to 95:5. For example, in various embodiments, the weight ratio of monoglyceride (1-monoglyceride and/or 2-monoglyceride) to diglyceride (1,2-diglyceride and/or 1,3-diglyceride) is from about 65:35 to about 95:5, or from about 70:30 to from about 90:10.

II. Methods of Preparation

The alkoxylated mono and diglycerides of the invention can be prepared by procedures known to those skilled in the art. Examples of various glycerolysis methods are shown in a review article (Norman Sonntag, JAOCS, vol. 59, No. 10 Oct. 1982, Page 795A-802A). Most commonly they are obtained by a trans esterification process which reacts glycerine with triglycerides or fatty acids followed by alkoxylation. They can also be obtained by alkoxylating glycerine first then followed by esterification with fatty acids or fatty acid esters.

Sonntag describes a variety of glycerolysis methods, including batch-type processes. These methods are described as generally including (a) use of heat and agitation to maximize solubility of glycerol in the fatty phases, (b) use of excess glycerol over the theoretical requirement of 2 moles, and removal of excess glycerol at the end of the glycerolysis, (c) use of a catalyst/emulsifier system, and (d) catalyst neutralization after completion of the reaction and before removal of excess glycerol and cooling.

One consideration described as affecting the practical success of glycerolysis is establishing a sufficient degree of homogeneity, or solubility of the glycerol in the initial triglyceride fat or in subsequent fat-like phases. Glycerol is not soluble in common fats to a degree that allows for the molar excess of glycerol to react to completion at room temperature. Accordingly, elevated temperatures (e.g., temperatures in excess of about 200° C., in excess of about 220° C., or about 240° C.) are typically used to increase the solubility of glycerol and drive the reaction to completion. The upper temperature limit may depend on a variety of factors. For example, undesired by-products (e.g., acrolein) may be formed at temperatures in excess of 255° C., or in excess of 260° C. Agitation may also be utilized to promote solubility of the glycerol. Neither the manner nor degree of agitation are narrowly critical, and may be selected by one skilled in the art in view of the particular reaction conditions.

Glycerolyses are typically catalyzed, often using alkaline catalysts (e.g., NaOH, KOH, Ca(OH)$_2$, CaO, SrO), the sodium salts of lower aliphatic alcohols (e.g., methanol and ethanol), and acids. Various metals such as Na, K, or Sn may also be utilized as catalysts. Generally, alkaline catalysts are preferred. More particularly, due to their effectiveness and low cost, NaOH and KOH are generally preferred as catalysts for industrial glycerolyses. Since the catalyst increases the reaction rate, the presence of the catalyst may increase reversion of the desired monoglycerides back to reactant form. This reversion may be minimized by relatively rapid neutralization of the catalyst, cooling of the reaction mixture and/or removal of the glycerol at the end of the desired reaction period.

Sonntag also describes and/or lists a variety of batch and continuous glycerolysis methods known in the art including, for example, U.S. Pat. Nos. 4,025,540; 4,950,441; and 6,723,863, the entire contents of which are incorporated by reference herein for all relevant purposes. Batch-type glycerolysis methods include those described in U.S. Pat. Nos. 1,505,560; 2,197,339; 2,197,340; 2,206,167; 2,206,168; 2,748,354; 2,496,328; 2,909,540; and 3,083,216, the entire contents of which are incorporated herein by reference for all relevant purposes. Continuous glycerolysis methods include those described in U.S. Pat. Nos. 2,383,581; 2,474,740; 2,634,278; 2,634,279; 2,875,221; 3,102,129; 3,095,431; 3,079,412; 3,313,834; and 4,950,441, the entire contents of which are incorporated by reference herein for all relevant purposes.

Further in accordance with the foregoing, the relative proportions of glycerol and fatty acids may be selected to provide a desired mixture of glycerides (e.g., 1-monoglyceride, 2-monoglyceride, 1,2-diglyceride, and/or 1,3-diglyceride).

It is to be understood that glycerolysis in connection with preparation of the alkoxylated glycerides of the present invention may be conducted in accordance with the preceding discussion, and utilizing other methods known in the art.

As noted, the alkoxylated glycerides of the present invention may generally be prepared by a process that includes trans esterification followed by alkoxylation or alkoxylation followed by esterification. Regardless of the order of alkxoylation and esterification, alkoxylation to prepare the alkoxylated glycerides of the present invention is generally conducted in accordance with conventional methods known in the art. Alkoxylation generally comprises a condensation reaction between an alkylene oxide and an organic compound containing at least one active hydrogen (i.e., glycerol or an ester thereof) in the presence of a catalyst. A wide variety of catalysts are well-known for use in alkoxylation processes including, for example, various acidic and alkaline catalysts (e.g., potassium hydroxide). Various alkoxylation methods are well-known in the art including, for example, those described in U.S. Pat. Nos. 4,754,075; 5,114,900; and 5,120,697. The conditions of suitable alkoxylation methods are well-known in the art. For example, the temperature of the reaction is typically sufficient to provide a suitable rate of reaction, but without undesired degradation of the reactants or reaction products. Generally, alkoxylation temperatures can range from about 50° C. to about 270° C., or from about 100° C. to about 200° C. The pressure of the alkoxylation reaction is not narrowly critical. Typically, the alkoxylation medium is agitated to promote dispersion of the reactants and catalyst throughout.

III. Herbicidal Formulations

The herbicidal formulations of the present invention can, in addition to the surfactants set forth in the above formula, contain additional components including, but not limited to, additional surfactants or other additives. It is preferred that when the formulations of the invention do contain such additional components, that such additional components are substantially non-irritating to the eye, substantially non-toxic to aquatic life, and have acceptable bio-efficacy. Herbicidal formulations of the present inventions may be in the form of liquid concentrates, solid concentrates, or a "ready-to-use" (i.e., RTU) composition prepared by diluting an aqueous concentrate or dissolving a solid composition.

Surfactants

Additional components of the formulations of the present invention include surfactants such as cationic, anionic, nonionic, and amphoteric surfactants. These surfactants include those disclosed in Cutcheon's Emulsifier and Detergents, North America Edition, 2006.

Non-limiting examples of preferred cationic surfactants are alkoxylated alkylamine and its quaternary derivative, alkoxylated etheramine and its quaternary derivative, alkoxylated alkyl amine oxide, alkoxylated alkyl etheramine oxide, alkyl amidopropyl amine oxide, alkyl trimethyl ammonium chloride, and alkyl (preferably $C_6$ to $C_{10}$) dimethylamidopropylamine.

Non-limiting examples of preferred anionic surfactants are alkylsulfate, alkylethersulfate, alkylsulfonate, alkylsulfosuccinate, alkoxylated phosphate ester, alkyl alpha olefin sulfonate, alkyl n-methyl taurate, fatty acid isethionate, and alkyl ether carboxylate. Non-limiting examples of preferred nonionic surfactants are sorbitan ester and its alkoxylated derivative, sorbitol ester and its alkoxylated derivative, fatty acid ester, castor oil alkoxylate, alcohol alkoxylate, alkanolamide, alkanolamide alkoxylate, and alkyl polyglycoside.

Non-limiting examples of preferred amphoteric surfactants are alkyl betaine, alkyl amidopropyl betaine, alkylamphoacetate, alkylamphodiacetate, alkylamphocarboxylate, alkylamphopropionate, alkylamphodipropionate, alkyl amidoamine carboxylate, alkylamphohydroxypropyl sulfonate, alkyl sultaine, alkyl amidopropyl hydroxyl sultaine, alkyl dihydroxyethyl glycinate, and alkyl aminopropionate.

In various embodiments, the weight ratio of alkoxylated glyceride(s) to total surfactant concentration of the formulation is generally from about 1:8 to about 1:1, typically from about 1:4 to about 1:1 and, more typically, from about 1:2 to about 1:1. The weight ratio of alkoxylated monoglyceride (1-monoglyceride and/or 2-monoglyceride) to total surfactant concentration is typically from about 1:32 to about 1:1 and, more typically, from about 1:16 to about 1:1. In these and various other embodiments, the weight ratio of alkoxylated diglycerides (1,2-diglyceride and/or 1,3-diglyceride) to total surfactant concentration is typically from about 1:32 to about 1:1 and, more typically, from about 1:16 to about 1:1.

In various embodiments, the ethoxylated glyceride includes a substantial fraction of monoglycerides or diglycerides. For example, the weight ratio of alkoxylated monoglyceride(s) to alkoxylated diglyceride(s) may be from about 1:99 to about 99:1. Thus, in various embodiments, the weight ratio of alkoxylated monoglyceride(s) to alkoxylated diglyceride(s) is at least about 70:30, at least about 80:20, at least about 90:10, or at least about 95:5. Alternatively, in various other embodiments, the weight ratio of alkoxylated diglyceride(s) to alkoxylated monoglyceride(s) is at least about 70:30, at least about 80:20, at least about 90:10, or at least about 95:5.

Further in accordance with the foregoing, detailed below are various particular types of surfactants suitable for use in the formulations of the present invention.

Alkoxylated Tertiary Amines

In some embodiments, the herbicidal composition comprises a surfactant component comprising a surfactant selected from among an alkoxylated tertiary amine, an alkoxylated quaternary amine, or a combination thereof.

Alkoxylated tertiary amine surfactants for use in the compositions of the present invention have the general Structure (I):

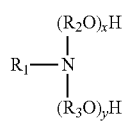

Structure (I)

wherein $R_1$ is a hydrocarbyl or substituted hydrocarbyl having an average number of carbon atoms in the population of molecules within about 4 to about 22 carbon atoms, $R_2$ and $R_3$ are each independently hydrocarbylene having 2, 3, or 4 carbon atoms, and the sum of x and y is an average value ranging from about 1 to about 50.

$R_1$ is preferably an alkyl having an average number of carbon atoms ranging from about 4 to about 22 carbon atoms, more preferably from about 8 to about 22 carbon atoms, and still more preferably from about 10 to about 20 carbons atoms, for example coco, tallow, oleyl, and stearyl. $R_2$ and $R_3$ are preferably ethylene or propylene. The sum of x and y is preferably an average value ranging from about 1 to about 25.

Specific alkoxylated tertiary amine co-surfactants for use in the herbicidal compositions of the present invention include, for example, Ethomeen T/12, Ethomeen T/15, Ethomeen T/20, Ethomeen T/25, Ethomeen T/30, Ethomeen T/60, Ethomeen HT/12, Ethomeen HT/40, Ethomeen HT/60, Ethomeen C/12, Ethomeen C/15, Ethomeen C/25, Ethomeen O/12, Ethomeen OV/17, Ethomeen S/12, Ethomeen S/17, and Ethomeen S/22, each of which are available from Akzo Nobel.

Alkylamine Alkoxylates/Etheramine Alkoxylates

In some embodiments, the herbicidal composition comprises a surfactant component comprising a combination of an alkylamine alkoxylate surfactant having a high degree of alkoxylation and an etheramine alkoxylate surfactant.

The alkylamine alkoxylate surfactant having a high degree of alkoxylation is of Structure (II):

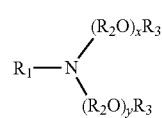

Structure (II)

wherein $R_1$ is a straight or branched chain $C_{12}$ to $C_{18}$ hydrocarbyl group (e.g., tallow, soya, coco or oleyl), more preferably a mixture of straight or branched chain $C_{14}$ to $C_{18}$ hydrocarbyl groups, still more preferably a mixture of straight or branched chain $C_{16}$ to $C_{18}$ alkyl (tallow), $R_2$ is $C_1$ to $C_4$ alkylene, more preferably $C_2$, each $R_3$ is independently hydrogen or $C_1$ to $C_6$ alkyl, preferably hydrogen, and, in some embodiments, x and y are average numbers such that x+y is in the range of from about 5 to about 25, more preferably from about 5 to about 20, more preferably from about 8 to about 20, more preferably from 8 to about 15, and still more preferably from about 9 to about 10. In other embodiments, x and y are average numbers such that x+y is greater than 5, such as in the range of from 6 to about 15, from 6 to about 12, or from 6 to about 10. Examples of suitable surfactants include, without restriction, Berol 300 (cocoamine 5EO), Berol 381 (tallowamine 15EO), Berol 391 (tallowamine 5EO), Berol 397 (cocoamine 15 EO), Berol 398 (cocoamine 11 EO), Berol 498 (tallowamine 10 EO), Ethomeen C/15 (cocoamine 5EO), Ethomeen C/25 (cocoamine 15 EO), Ethomeen T/15 (tallowamine 5EO), Ethomeen T/20 (tallowamine 10EO), Ethomeen T/19 (tallowamine 9EO), Ethomeen T/25 (tallowamine 15 EO), Witcamine TAM-105 (tallowamine 10 EO), Witcamine TAM-80 (tallowamine 8 EO), Witcamine TAM-60 (tallowamine 6EO), all available from Akzo Nobel.

The etheramine alkoxylate surfactant is of Structure (III):

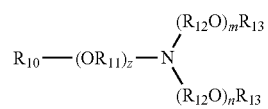

Structure (III)

wherein $R_{10}$ is a straight or branched chain $C_6$ to $C_{22}$ hydrocarbyl group (e.g., tallow, soya, coco or oleyl), more preferably a mixture of straight or branched chain $C_{12}$ to $C_{18}$ alkyl, more preferably a mixture of straight or branched chain $C_{12}$ to $C_{16}$ alkyl, more preferably a mixture of straight or branched chain $C_{12}$ to $C_{14}$ alkyl, $R_{11}$ is $C_1$ to $C_4$ alkylene, more preferably $C_3$ alkylene, z is an average number of from 1 to about 10, more preferably from about 1 to about 5, and still more preferably about 2, $R_{12}$ is $C_1$ to $C_4$ alkylene, more preferably $C_2$, m and n are average numbers such that m+n is in the range of from 2 to about 60, preferably from about 2 to about 20, from about 5 to about 15, from about 2 to about 10, from about 5 to about 10, more preferably about 5, and each $R_{13}$ is independently hydrogen or $C_1$ to $C_6$ alkyl, preferably hydrogen. When combined with the water-soluble herbicide potassium glyphosate, m and n are average numbers such that m+n is in the range of from about 5 to about 8. When combined with a water-soluble salt of glyphosate other than the potassium salt, m and n are average numbers such that m+n is in the range of from about 5 to about 8. Examples of suitable surfactants include, without restriction, Tomamine E-14-2 (bis-(2-hydroxyethyl)isodecyloxypropylamine), Tomamine E-14-5 (poly-(5)oxyethylene isodecyloxypropylamine), Tomamine E-17-2 (bis-(2-hydroxyethyl) isotridecyloxypropylamine), Tomamine E-17-5 (poly (5)oxyethylene isotridecyloxypropylamine), Tomamine E-19-2 (bis-(2-hydroxyethyl)linear alkyloxypropylamine) all available from Air Products, and Surfonic AGM-550 (where $R_{10}$ is $C_{12\text{-}14}$, $R_{11}$ is isopropyl, $R_{12}$ is $C_2$ and the sum of m and n is 5) available from Huntsman.

The weight ratio of the etheramine alkoxylate surfactant to the alkylamine alkoxylate surfactant having a high degree of alkoxylation is from about 90:10 to about 10:90, preferably from about 80:20 to about 40:60, more preferably from about 80:20 to about 50:50. In some preferred embodiments, the ratio is not greater than about 70:30, for example from about 70:30 to about 50:50. The weight ratio of glyphosate a.e. to total surfactant of from about 1:1 to about 6:1, preferably from about 3:1 to about 5:1, more preferably from about 4:1 to about 4.5:1. The preferred ratios are generally based on a balance between optimum biological and cost performance. With less etheramine surfactant a loss of weed control begins to be observed and with more the increase in weed control does not offset the additional cost of the formulation.

Alkoxylated Tertiary Etheramines

In some embodiments, the herbicidal composition comprises a surfactant component comprising a surfactant selected from among alkoxylated tertiary etheramine surfactants, alkoxylated quaternary etheramine surfactants, and combinations thereof.

Alkoxylated tertiary etheramine surfactants for use in the herbicidal compositions of the present invention have the general Structure (IV):

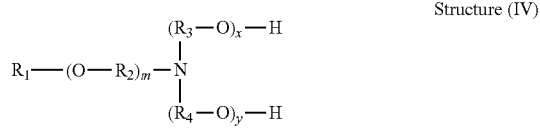

Structure (IV)

wherein $R_1$ is a hydrocarbyl or substituted hydrocarbyl having an average number of carbon atoms in the population of molecules within about 4 to about 22 carbon atoms; $R_2$, $R_3$ and $R_4$ are each independently a hydrocarbylene having 2, 3, or 4 carbon atoms; m is an average number from about 1 to about 10; and the sum of x and y is an average value ranging from about 1 to about 60.

$R_1$ is preferably an alkyl having an average value ranging from about 4 to about 22 carbon atoms, more preferably from about 8 to about 22 carbon atoms, and still more preferably from about 10 to about 20 carbons atoms, for example coco, tallow, oleyl, and stearyl. Sources of the $R_1$ group include, for example, coco or tallow, or $R_1$ may be derived from synthetic hydrocarbyls, such as decyl, dodedecyl, tridecyl, tetradecyl, hexadecyl, or octadecyl groups. M is preferably from about 1 to 5, such as 2 to 3. $R_2$, $R_3$ and $R_4$ may independently be ethylene, propylene, isopropylene, and are preferably ethylene. The sum of x and y is preferably an average value ranging from about 1 to about 25.

Specific alkoxylated tertiary etheramine co-surfactants for use in the herbicidal composition of the present invention include, for example, any of the TOMAH E-Series surfactants, such as TOMAH E-14-2, TOMAH E-14-5, TOMAH E-17-2, TOMAH E-17-5, TOMAH E-19-2, TOMAH E-18-2, TOMAH E-18-5, TOMAH E-18-15, TOMAH E-S-2, TOMAH E-S-15, TOMAH E-T-2, TOMAH E-T-5, and TOMAH E-T-15, all available from Air Products and Chemicals, Inc. Another example is SURFONIC AGM 550 available from Huntsman Petrochemical Corporation.

Alkoxylated Tertiary Amine Oxide Surfactants

Alkoxylated tertiary amine oxide surfactants for use in the herbicidal compositions of the present invention have the general Structure (V):

Structure (V)

wherein $R_{31}$ is a hydrocarbyl or substituted hydrocarbyl having from about 4 to about 22 carbon atoms, $R_{32}$ and $R_{33}$ are each independently hydrocarbylene having 2, 3, or 4 carbon atoms, and the sum of x and y is an average value ranging from about 2 to about 50.

$R_{31}$ is preferably an alkyl having from about 4 to about 22 carbon atoms, more preferably from about 8 to about 18 carbon atoms, and still more preferably from about 12 to about 18 carbons atoms, for example coco or tallow. $R_{31}$ is most preferably tallow. $R_{32}$ and $R_{33}$ are preferably ethylene. The sum of x and y is preferably an average value ranging from about 2 to about 22, more preferably between about 10 and about 20, for example, about 15.

Specific alkoxylated tertiary amine oxide surfactants for use in the herbicidal compositions of the present invention include, for example, any of the AROMOX series of surfactants, including AROMOX C/12, AROMOX C/12W, AROMOX DMC, AROMOX DM16, AROMOX DMHT, and AROMOX T/12 DEG.

Mono-Alkoxylated Tertiary Amine Surfactants

In some embodiments, the herbicidal composition comprises a surfactant component comprising a mono-alkoxylated tertiary amine surfactants having the general Structure (VI):

Structure (VI)

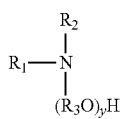

wherein $R_1$ and $R_2$ are each independently hydrocarbyl or substituted hydrocarbyl having an average number of carbon atoms in the population of molecules within about 4 to about 22 carbon atoms, $R_3$ is a hydrocarbylene having 2, 3, or 4 carbon atoms, and y is an average value ranging from about 1 to about 25.

$R_1$ are $R_2$ are preferably an alkyl having an average value ranging from about 4 to about 22 carbon atoms, more preferably from about 8 to about 22 carbon atoms, and still more preferably from about 10 to about 20 carbons atoms, for example coco, tallow, oleyl, and stearyl. $R_2$ is preferably ethylene or propylene.

Peaked Distribution Alkoxylated Alkylamine Surfactants

More particularly, the herbicidal formulation may comprise an alkloxylated alkylamine of the type described in International Publication No. WO 2007/109791 (Alkoxylated Alkylamine/Alkyl Ether Amines with Peaked Distribution) and WO 2006/034459 (Alkoxylated Alkylamine/Alkyl Ether Amines with Peaked Distribution), the entire contents of which are incorporated herein by reference for all relevant purposes.

For example, in various embodiments the formulation comprises a surfactant comprising an ethoxylated alkyl(ether)amine with peaked distribution, the ethoxylated alkyl(ether)amine with peaked distribution characterized by a degree of peaking that is at least 5% higher than that of the conventional non-peaked ethoxylated alkyl(ether)amines having the same carbon-chain length and average EO chain length prepared via conventional base catalysis. Conventional base catalysis comprises NaOH-catalyzed reaction of $RNH_2$ with alkylene oxide conducted entirely under autogenous pressure up to 90 psig (621 kPa) at a catalyst concentration of 0.2 wt. % and a temperature between 160° C. and 180° C.

In still further embodiments, the formulation comprises a polyalkoxylated alkyl(ether)amine substituted with two alkylene oxide chains in peaked distribution and containing an average total of at least about 6 alkylene oxide units per molecule. The peaked distribution alkoxylated alkyl(ether)amine is generally characterized by a degree of peaking that is at least 5% higher than that of the conventional non-peaked alkoxylated alkyl(ether)amines having the same carbon-chain length and average alkylene oxide chain length prepared via conventional base catalysis.

Further in accordance with the present invention, along with the alkoxylated glyceride(s), the formulation may comprise an alkoxylated alkyl(ether)amine surfactant (including peaked distribution alkoxylated alkyl(ether)amine surfactants) comprising a mixture of homologs corresponding to Structure (VII):

Structure (VII)

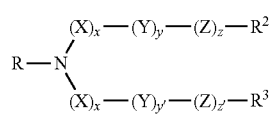

wherein X, Y and Z are alkylene oxide groups containing 2-3 carbon atoms, x is one, each of y, y', z and z' is an integer independently varying from 0-20, the sum of (y+y'+z+z')≥1, each of $R^2$ and $R^3$ is independently selected from the group consisting of hydrogen, methyl and ethyl, and R is selected from: (i) a linear or branched, saturated or non-saturated alkyl group containing 12-22 carbon atoms and derived from a primary amine having a molecular weight of at least 200, and (ii) a group of the formula:

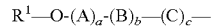

where $R^1$ is a linear or branched, saturated or non-saturated alkyl group containing 12-22 carbon atoms, each of A and B is an alkylene oxide group, and C is alkylene group containing 2-4 carbon atoms, a and b each varies from 0-5, and c is 1. For example, herbicidal formulations of the present invention may comprise peaked distribution surfactants of formula (I) characterized by a degree of peaking that is at least 5% higher than that of the conventional non-peaked ethoxylated alkyl(ether)amines having the same carbon-chain length and average EO chain length prepared via conventional base catalysis (as defined elsewhere herein).

Generally, aqueous concentrate herbicidal formulations including an alkoxylated (e.g., ethoxylated) alkyl(ether)amine surfactant contain not more than 4 wt. %, not more than 3 wt. %, not more than 2 wt. %, not more than 1 wt. %, not more than about 0.5 wt. %, or not more than about 0.2 wt. % vinyl polyethylene glycols. Additionally or alternatively, alkoxylated alkyl(ether)amine surfactants included in aqueous concentrate herbicidal formulations of the present invention contain not more than 4 wt. %, not more than 3 wt. %, not more than 2 wt. %, not more than 1 wt. %, not more than about 0.5 wt. %, or not more than about 0.2 wt. % vinyl polyethylene glycols. Furthermore, aqueous concentrate herbicidal formulations including an alkoxylated (e.g., ethoxylated) alkyl(ether)amine surfactant typically contain not more than about 5 wt. %, not more than about 4 wt. %, or not more than about 3 wt. % (poly)ethylene glycol derivatives (EGDs). In accordance with these and various other preferred embodiments, alkoxylated alkyl(ether)amine surfactants included in aqueous concentrate herbicidal formulations of the present invention typically contain not more than 4 wt. %, not more than 3 wt. %, not more than 2 wt. %, not more than 1 wt. %, not more than about 0.5 wt. %, or not more than about 0.2 wt. % vinyl polyethylene glycols.

Typically, the weight ratio of alkoxylated glyceride(s) to the total proportion of alkoxylated alkyl(ether)amine surfactant(s) (peaked distribution or otherwise) is from about 0.5:1 to about 25:1, from about 0.5:1 to about 20:1, from about 1:1 to about 20:1, from about 1:1 to about 10:1, from about 1:1 to about 8:1, or from about 1:1 to about 5:1. For example, in various embodiments the weight ratio of alkoxylated glycerides to the total proportion of ethoxylated alkyl(ether)amines with peaked distribution is typically from about 0.5:1 to about 25:1, more typically from about 0.5:1 to about 20:1, still more typically from about 1:1 to about 20:1 and, even more typically, from about 1:1 to about 10:1 (e.g., from about 1:1 to about 8:1, or from about 1:1 to about 5:1). Additionally or alternatively, the weight ratio of alkoxylated glyceride(s) to the proportion of a peaked distribution alkoxylated alkyl(ether)amine surfactant is generally from about 0.5:1 to about 25:1, typically from about 0.5:1 to about 20:1, or from about 1:1 to about 10:1.

In various further embodiments, the weight ratio of alkoxylated monoglyceride(s) (1-monoglyceride and/or 2-monoglyceride) to one or more peaked distribution alkoxylated alkyl(ether)amine surfactants is from about 0.1:1 to about 20:1, typically from about 0.1:1 to about 10:1 and, more typically, from about 0.25:1 to about 5:1. In still further embodiments, the weight ratio of alkoxylated diglyceride(s) (1,2-diglyceride and/or 1,3-diglyceride) to one or more peaked distribution alkoxylated alkyl(ether)amine surfactant is generally from about 0.1:1 to about 20:1, typically from about 0.1:1 to about 10:1 and, more typically, from about 0.25:1 to about 5:1. Additionally or alternatively, formulations of the present invention may comprise alkoxylated monoglycerides and diglycerides along with alkoxylated alkyl(ether)amine surfactants that do not exhibit peaked distribution within the noted ratios.

Generally in accordance with these embodiments the weight ratio of glyphosate (a.e.) to total surfactant concentration is from about 25:1 to about 0.5:1, from about 20:1 to about 1:1, or from about 8:1 to about 1.5:1.

Preferably in accordance with these embodiments, the formulation, ethoxylated alkyl(ether)amine, polyalkoxylated alkyl(ether)amine, and/or alkoxylated alkyl(ether)amine surfactant contains not more than about 4 wt. %, not more than about 3 wt. %, not more than about 2 wt. %, not more than 1 wt. %, not more than about 0.5 wt. %, or not more than about 0.2 wt. % vinyl polyethylene glycols. Additionally or alternatively, preferably the formulation, ethoxylated alkyl(ether)amine, polyalkoxylated alkyl(ether)amine, and/or alkoxylated alkyl(ether)amine surfactant contains not more than about 5 wt. %, not more than about 4 wt. %, or not more than about 3 wt. % (poly)ethylene glycol derivatives (EGDs).

The cloud points of alkoxylated alkylamine-containing formulations, as determined using conventional means known in the art, are typically at least about 50° C., at least about 55° C., at least about 60° C., or at least about 65° C.

Alkoxylated Polyamines

An example of an alkoxylated polyamine surfactant for use in the herbicidal compositions of the present invention is a surfactant having the general Structure (VIII):

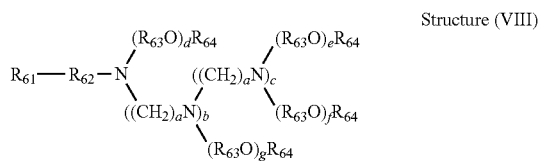

Structure (VIII)

wherein $R_{61}$ is an alkyl or alkenyl radical containing 6 to 25 carbon atoms and from 0 to 3 carbon-carbon double bonds; $R_{62}$ is $-OCH_2CH_2CH_2-$, $-C(=O)OCH_2CH_2CH_2-$, $-C(=O)NHCH_2CH_2CH_2-$, or $-CH_2-$; each occurrence of $R_{64}$ is independently $-H$, $-OC(=O)R_1$, $-SO_3^-A^+$ or $-CH_2C(=O)O^-A^+$ wherein $A^+$ is an alkali metal cation, ammonium or $H^+$; each occurrence of a is from 3 to 8; each $R_{63}$ is independently ethyl, isopropyl or n-propyl; d, e, f and g are each independently from 1 to 20, b is from 0 to 10, c is 0 or 1, the sum of (c+d+e+f) is from (3+b) to 20, and the molecular weight is no more than about 800. The surfactants of formula (7) can optionally be in the form of a cation where one or more nitrogen atoms is additionally substituted with hydrogen, methyl, ethyl, hydroxyethyl or benzyl and one or more anions, equal in number to the number of said additionally substituted nitrogen atoms and being selected from chloride, methylsulfate and ethylsulfate. The surfactants of Structure (VIII) can further optionally be in the form of amine oxides.

Examples of specific alkoxylated polyamine surfactants for use in the herbicidal composition of the present invention are described in described in U.S. Pat. No. 6,028,046 (to Arif). Alkoxylated polyamine surfactants include, for example, ethoxylates of N-coco propylene diamine (e.g., Adogen 560 available from Evonik) containing an average of from 2EO to 20EO, for example, 4.8, 10 or 13.4EO; ethoxylates of N-tallow propylene diamine (e.g., Adogen 570 available from Evonik) containing an average of form 2EO to 20EO, for example, 13EO; and ethoxylates of N-tallow propylene triamine (e.g., Adogen 670 available from Evonik) containing an average of from 3EO to 20EO, for example, 14.9EO.

Other polyamine surfactants for use in the herbicidal compositions of the present invention have the general Structure (IX):

Structure (IX)

wherein $R_{71}$ is $C_{8-20}$, $R_{72}$ is $C_{1-4}$ and n is 2 or 3. Examples of polyamines for use in the compositions and methods of the present invention include Triamine C ($R_{71}$ is coco ($C_{10-14}$)), $R_{72}$ is $C_3$, n is 2 and amine number (total mg KOH/g) is 500-525), Triamine OV ($R_{71}$ is oleyl (vegetable oil), $R_{72}$ is $C_3$, n is 2 and amine number (total mg KOH/g) is 400-420), Triamine T ($R_{71}$ is tallow ($C_{16-18}$), $R_{72}$ is $C_3$, n is 2 and amine number (total mg KOH/g) is 415-440), Triamine YT ($R_{71}$ is tallow ($C_{16-18}$), $R_{72}$ is $C_3$, n is 2 and amine number (total mg KOH/g) is 390-415), Triameen Y12D ($R_{71}$ is dodecyl ($C_{12}$), $R_{72}$ is $C_3$, n is 2 and amine number (total mg HCl/g is 112-122), Triameen Y12D-30 ($R_{71}$ is dodecyl ($C_{12}$), $R_{72}$ is $C_3$, n is 2 and amine number (total mg HCl/g is 335-365), Tetrameen OV ($R_{71}$ is oleyl (vegetable oil), $R_{72}$ is $C_3$, n is 3 and amine number (total mg KOH/g) is 470-500), Tetrameen T ($R_{71}$ is tallow ($C_{16-18}$), $R_{72}$ is $C_3$, n is 3 and amine number (total mg KOH/g) is 470-495), wherein each is available from Akzo Nobel.

Alkoxylated Quaternary Amines

Alkoxylated quaternary amine surfactants for use in the compositions of the present invention have the general Structure (X):

Structure (X)

wherein $R_1$, $R_2$, $R_3$, x and y are as described above for the alkoxylated tertiary amine surfactants of Structure (I), i.e., wherein $R_1$ is a hydrocarbyl or substituted hydrocarbyl having an average number of carbon atoms in the population of molecules within about 4 to about 22 carbon atoms, $R_2$ and $R_3$ are each independently hydrocarbylene having 2, 3, or 4 carbon atoms, and the sum of x and y is an average value ranging from about 1 to about 50. $R_4$ is preferably a hydrocarbyl or substituted hydrocarbyl having from 1 to about 4 carbon atoms, more preferably methyl. X is a charge balancing counter-anion, such as sulfate, chloride, bromide, nitrate, among others.

$R_1$ is preferably an alkyl having an average number of carbon atoms ranging from about 4 to about 22 carbon atoms, more preferably from about 8 to about 22 carbon atoms, and still more preferably from about 10 to about 20 carbons atoms, for example coco, tallow, oleyl, and stearyl.

$R_2$ and $R_3$ are preferably ethylene or propylene. The sum of x and y is preferably an average value ranging from about 1 to about 25.

Specific alkoxylated quaternary amine surfactants for use in the herbicidal composition of the present invention include, for example, Ethoquad O/12, Ethoquad T/12, Ethoquad T/15, Ethoquad T/20, Ethoquad T/25, Ethoquad HT/25, Ethoquad C/12, Ethoquad C/15, and Ethoquad C/25, each of which are available from Akzo Nobel.

Alkoxylated quaternary amine surfactants for use in the compositions of the present invention may also have the general Structure (XI):

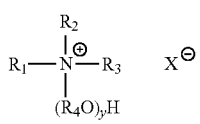

Structure (XI)

wherein $R_1$, $R_2$, and $R_3$ are each independently hydrocarbyl or substituted hydrocarbyl having an average number of carbon atoms in the population of molecules within about 4 to about 22 carbon atoms, $R_4$ is a hydrocarbylene having 2, 3, or 4 carbon atoms, and y is an average value ranging from about 1 to about 25. X is a charge balancing counter-anion, such as sulfate, chloride, bromide, nitrate, among others.

$R_1$, $R_2$, and $R_3$ are preferably alkyl having an average value ranging from about 4 to about 22 carbon atoms, more preferably from about 8 to about 22 carbon atoms, and still more preferably from about 10 to about 20 carbons atoms, for example coco, tallow, oleyl, and stearyl. R4 is preferably ethylene or propylene.

Further in accordance with the present invention, the herbicidal formulation may comprise an alkoxylated alkylamine quaternary amine surfactant including, for example, those described in International Publication No. WO 2006/034426, the entire contents of which are incorporated herein by reference for all relevant purposes. For example, the formulation may comprise at least one alkoxylated quaternary alkylammonium salt surfactant corresponding to the formula:

RR'N(+)AB where R is a straight chain or branched chain, saturated or unsaturated alkyl group having from 8 to 22 carbon atoms, R' is a straight or branched chain, saturated or unsaturated alkyl group having from 1 to 4 carbon atoms, A is $(R^2O)_p$ $(R^3O)_q(R^4O)_zR^8$ and B is $(R^5O)_p,(R^6O)_q,(R^7O)_z,R^9$ where each of $R^2$, $R^3$, $R^4$, $R^5$, $R^6$, and $R^7$ is independently selected from the group consisting of ethylene and isopropylene, each of $R^8$ and $R^9$ is selected from the group consisting of hydrogen, methyl and ethyl, and each of p, q, p', q', z and z' is independently an integer between 0 and 30 and the sum of p+p'+q+q'+z+z' is at least about 2. In accordance with these and various other embodiments, the formulation comprises at least one alkoxylated quaternary alkylammonium salt surfactant predominantly comprising an N-alkyl substituent derived from tallow.

Generally, the weight ratio of glyphosate (wt. % a.e.) to total surfactant concentration is from about 25:1 to about 0.5:1, from about 20:1 to about 1:1, or from about 8:1 to about 1.5:1.

Typically, the weight ratio of alkoxylated glycerides to alkoxylated quaternary alkylammonium salt surfactant(s) is from about 0.5:1 to about 25:1, from about 0.5:1 to about 20:1, from about 1:1 to about 20:1, from about 1:1 to about 10:1, from about 1:1 to about 8:1, or from about 1:1 to about 5:1.

Generally, the weight ratio of alkoxylated monoglyceride (1-monoglyceride and/or 2-monoglyceride) to alkoxylated quaternary alkylammonium salt surfactant(s) is from about 1:1 to about 20:1, typically from about 1:1 to about 10:1 and, more typically, from about 1:1 to about 5:1. In various other embodiments, the weight ratio of alkoxylated diglyceride (1,2-diglyceride and/or 1,3-diglyceride) to alkoxylated quaternary alkylammonium salt surfactant may also generally be from about 1:1 to about 20:1, typically from about 1:1 to about 10:1 and, more typically, from about 1:1 to about 5:1.

Alkoxylated Quaternary Etheramines

Alkoxylated quaternary etheramine surfactants for use in the herbicidal compositions of the present invention have the general Structure (XII):

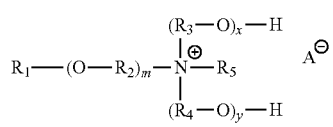

Structure (XII)

wherein $R_1$ is a hydrocarbyl or substituted hydrocarbyl having an average number of carbon atoms in the population of molecules within about 4 to about 22 carbon atoms; $R_2$, $R_3$ and $R_4$ are each independently is a hydrocarbylene having 2, 3, or 4 carbon atoms; m is an average number from about 1 to about 10; and the sum of x and y is an average value ranging from about 1 to about 60. $R_5$ is preferably a hydrocarbyl or substituted hydrocarbyl having from 1 to about 4 carbon atoms, more preferably methyl. A is a charge balancing counter-anion, such as sulfate, chloride, bromide, nitrate, among others.

$R_1$ is preferably an alkyl having an average value ranging from about 4 to about 22 carbon atoms, more preferably from about 8 to about 22 carbon atoms, and still more preferably from about 10 to about 20 carbons atoms, for example coco, tallow, oleyl, and stearyl. Sources of the $R_1$ group include, for example, coco or tallow, or $R_1$ may be derived from synthetic hydrocarbyls, such as decyl, dodedecyl, tridecyl, tetradecyl, hexadecyl, or octadecyl groups. M is preferably from about 1 to 5, such as 2 to 3. $R_2$, $R_3$ and $R_4$ may independently be ethylene, propylene, isopropylene, and are preferably ethylene. $R_5$ is preferably methyl. The sum of x and y is preferably an average value ranging from about 1 to about 25.

Specific alkoxylated quaternary etheramine co-surfactants for use in the herbicidal composition of the present invention include, for example, TOMAH Q-14-2, TOMAH Q-17-2, TOMAH Q-17-5, TOMAH Q-18-2, TOMAH Q-S, TOMAH Q-S-80, TOMAH Q-D-T, TOMAH Q-DT-HG, TOMAH Q-C-15, and TOMAH Q-ST-50, all available from Air Products and Chemicals, Inc.

Sulfate Surfactants

Sulfate surfactants for use in the herbicidal compositions of the present invention have the general Structure (XIIIa-c):

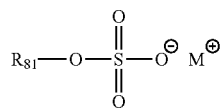

Structure (XIIIa)

-continued

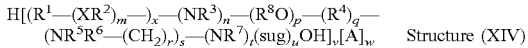
Structure (XIIIb)

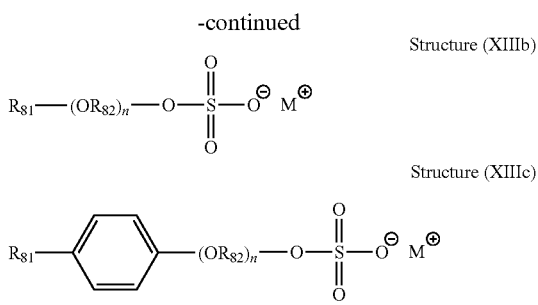
Structure (XIIIc)

wherein compounds of Structure (XIIIa) are alkyl sulfates, compounds of Structure (XIIIb) are alkyl ether sulfates and compounds of Structure (XIIIc) are alkyl aryl ether sulfates. $R_{81}$ is a hydrocarbyl or substituted hydrocarbyl having from about 4 to about 22 carbon atoms, each $R_{82}$ is independently ethyl, isopropyl or n-propyl and n is from 1 to about 20. M is selected from an alkali metal cation, ammonium, an ammonium compound or $H^+$. Examples of alkyl sulfates include sodium $C_{8-10}$ sulfate, sodium $C_{10-16}$ sulfate, sodium lauryl sulfate, sodium $C_{14-16}$ sulfate, diethanolamine lauryl sulfate, triethanolamine lauryl sulfate and ammonium lauryl sulfate. Examples of alkyl ether sulfates include sodium $C_{12-15}$ pareth sulfate (1 EO), ammonium $C_{6-10}$ alcohol ether sulfate (3 EO), sodium $C_{6-10}$ alcohol ether sulfate (3 EO), isopropylammonium $C_{6-10}$ alcohol ether sulfate (3 EO), ammonium $C_{10-12}$ alcohol ether sulfate (3 EO), sodium lauryl ether sulfate (3 EO). Examples of alkyl aryl ether sulfates include sodium nonylphenol ethoxylate sulfate (4 EO), sodium nonylphenol ethoxylate sulfate (10 EO), Witcolate™ 1247H ($C_{6-10}$, 3EO, ammonium sulfate), WITCOLATE 7093 ($C_{6-10}$, $_3$EO, sodium sulfate), WITCOLATE 7259 ($C_{8-10}$ sodium sulfate), WITCOLATE 1276 ($C_{10-12}$, 5EO, ammonium sulfate), WITCOLATE LES-60A ($C_{12-14}$, 3EO, ammonium sulfate), WITCOLATE LES-60C ($C_{12-14}$, 3EO, sodium sulfate), WITCOLATE 1050 ($C_{12-15}$, 10EO, sodium sulfate), WITCOLATE WAQ ($C_{12-16}$ sodium sulfate), WITCOLATE D-51-51 (nonylphenol 4EO, sodium sulfate) and WITCOLATE D-51-53 (nonylphenol 10EO, sodium sulfate).

Sulfonate Surfactants

Sulfonate surfactants for use in the herbicidal compositions of the present invention correspond to sulfate Structures (XIIIa) through (XIIIc) above except the R-substituted moiety is attached directly to the sulfur atom, for instance $R_{81}SO_3^-$. Examples of sulfonate surfactants include, for example, Witconate™ 93S (isopropylamine of dodecylbenzene sulfonate), WITCONATE NAS-8 (octyl sulfonic acid, sodium salt), WITCONATE AOS (tetradecyl/hexadecyl sulfonic acid, sodium salt), WITCONATE 60T (linear dodecylbenzene sulfonic acid, triethanolamine salt) and WITCONATE 605a (branched dodecylbenzene sulfonic acid, N-butylamine salt).

Derivatized Saccharide Surfactants/Amine Oxide Surfactants

In some preferred embodiments, the water-insoluble pesticide is dissolved in a surfactant component comprising a derivatized saccharide surfactant and an amine oxide surfactant. Among the derivatized saccharide surfactants, preferred classes include alkylpolysaccharides; alkylesters and alkoxylated alkylesters of saccharides; saccharide amines; silicone functionalized saccharide derivatives; and mixtures thereof. In some embodiments, wherein a mixture of derivatized saccharide surfactants is present, the surfactant mixture predominantly comprises one or more alkylpolysaccharides.

In some embodiments, alkylpolysaccharide surfactants suitable for use in herbicidal compositions of the present invention predominantly comprise one or more chemically stable surfactants having Structure (XIV):

Structure (XIV)

In reference to Structure (XIV), $R^1$ a straight or branched chain substituted or unsubstituted hydrocarbylene selected from alkyl, alkenyl, alkylphenyl, alkenylphenyl. Each X is independently an ether, thioether, sulfoxide, ester, thioester or amide linkage, each $R^2$ is independently $C_{2-6}$ hydrocarbylene, m is an average number of 0 to about 8, and x is an average number of 0 to about 6. The total number of carbon atoms in $R^1-(XR^2)_m$ is about 8 to about 24. $R^8$ is independently $C_2-C_4$ alkylene and p is an average number of 0 to about 12. $R^3$ is hydrogen or $C_{1-4}$ hydrocarbyl and n is 0 or 1. $R^4$ is $C_{1-4}$ hydrocarbyl or hydrocarbylene and q is 0 or 1. $R^5$ and $R^6$ are independently hydrogen or $C_{1-4}$ hydrocarbyl, r is 0 to 4 and s is 0 or 1. $R^7$ is hydrogen or $C_{1-4}$ hydrocarbyl and t is 0 or 1. A is an anionic entity, and v is an integer from 1 to 3 and w is 0 or 1 such that electrical neutrality is maintained.

In further reference to Structure (XIV), the sug moiety is a saccharide residue, and may be an open or cyclic (i.e., pyranose) structure. The saccharide may be a monosaccharide having 5 or 6 carbon atoms, a disaccharide, an oligosaccharide or a polysaccharide. Examples of suitable saccharide moieties, including their corresponding pyranose form, include ribose, xylose, arabinose, glucose, galactose, mannose, telose, gulose, allose, altrose, idose, lyxose, ribulose, sorbose (sorbitan), fructose, and mixtures thereof. Examples of suitable disaccharides include maltose, lactose and sucrose. Disaccharides, oligosaccharides and polysaccharides can be a combination of two or more identical saccharides, for example maltose (two glucoses) or two or more different saccharides, for example sucrose (a combination of glucose and fructose). The degree of polymerization, u, is an average number from 1 to about 10, from 1 to about 8, from 1 to about 5, from 1 to about 3, and from 1 to about 2.

In still further reference to Structure (XIV), when $R^1$ is a hydrophobic group and m, n, p, q, s and t are 0, $R^1$ is generally attached at the sug 1-position, but can be attached at the 2-, 3-, or 4-positions rather than the 1-position (thereby giving, e.g. a glucosyl or galactosyl as opposed to a glucoside or galactoside). For disaccharides and oligosaccharides, the additional saccharide units are generally attached to the previous saccharide unit's 2-position, but attachment through the 3-, 4-, and 6-positions can occur.

Optionally, the derivatized saccharide surfactant is an alkyl polysaccharide surfactant having Structure (XV):

$$R^{11}-O-(sug)_u \qquad \text{Structure (XV)}$$

wherein $R^{11}$ is a straight or branched chain substituted or unsubstituted hydrocarbyl selected from alkyl, alkenyl, alkylphenyl, alkenylphenyl having from about 4 to about 22 carbon atoms, preferably 4 to 18 carbon atoms, and wherein sug and u are as defined above. As known to those skilled in the art, as depicted in Structure (XV), $R^{11}$ is linked to a sug oxygen. In various particular embodiments, the polysaccharide surfactant may be an alkyl polyglucoside of Structure (XV) wherein: $R^{11}$ is a branched or straight chain alkyl group preferably having from 4 to 22 carbon atoms, more preferably from 8 to 18 carbon atoms, or a mixture of alkyl groups having an average value within the given range; sug is a glucose residue (e.g., a glucoside); and u is between 1 and about 5, and more preferably between 1 and about 3.

Examples of surfactants of Structure (XV) are known in the art. Representative surfactants are presented in Table I below wherein for each surfactant sug is a glucose residue.

TABLE I

| Trade name | $R^{11}$ | u |
|---|---|---|
| APG 225 | $C_{8-12}$ alkyl | 1.7 |
| APG 325 | $C_{9-11}$ alkyl | 1.5 |
| APG 425 | $C_{8-16}$ alkyl | 1.6 |
| APG 625 | $C_{12-16}$ alkyl | 1.6 |
| GLUCOPON 600 | $C_{12-16}$ alkyl | 1.4 |
| PLANTAREN 600 | $C_{12-14}$ alkyl | 1.3 |
| PLANTAREN 1200 | $C_{12-16}$ alkyl | 1.4 |
| PLANTAREN 1300 | $C_{12-16}$ alkyl | 1.6 |
| PLANTAREN 2000 | $C_{8-16}$ alkyl | 1.4 |
| Agrimul PG 2076 | $C_{8-10}$ alkyl | 1.5 |
| Agrimul PG 2067 | $C_{8-10}$ alkyl | 1.7 |
| Agrimul PG 2072 | $C_{8-16}$ alkyl | 1.6 |
| Agrimul PG 2069 | $C_{9-11}$ alkyl | 1.6 |
| Agrimul PG 2062 | $C_{12-16}$ alkyl | 1.4 |
| Agrimul PG 2065 | $C_{12-16}$ alkyl | 1.6 |
| BEROL AG6202 | 2-ethyl-1-hexyl | |

One such surfactant of the general Structure (XV) has the following Structure (XVA):

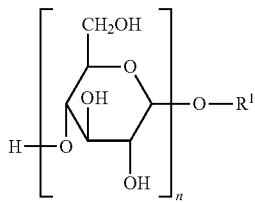

Structure (XVA)

wherein n is the degree of polymerization and is typically within the range from 1 to 3, for example from 1 to 2, and $R^1$ is a branched or straight chain alkyl group having from 4 to 18 carbon atoms or a mixture of alkyl groups having an average value within the given range.

In some embodiments, the derivatized saccharides are fatty acid esters of a saccharide, disaccharide, oligosaccharide or polysaccharide as depicted in Structure (XVIA) or (XVIB):

 Structure (XVIA)

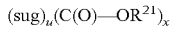 Structure (XVIB)

wherein: sug is as defined above; $R^{21}$ is a straight or branched chain alkyl or alkenyl group having from about 4 to about 22 carbon atoms; u is 1 to about 10; and x is a multiple of u with the average number being from about 1 to about 5, for example, 1.5. Preferred are sucrose or sorbitan sug units, $R^{21}$ having from about 8 to about 18 carbons, u=1, and x=about 1 to about 5. Examples include sorbitan monolaurate (Emsorb 2515), sorbitan monooleate (Emsorb 2500), sorbitan triooleate (Emsorb 2503), sorbitan sesquioleate (Emsorb 2502).

In other embodiments, the derivatized saccharides are alkoxylated fatty acid esters of a saccharide, disaccharide, oligosaccharide or polysaccharide as depicted in Structure (XVII):

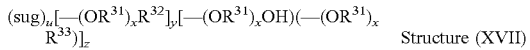 Structure (XVII)

wherein: sug is as defined above; each $R^{31}$ is independently an alkyl having from 2 to about 4 carbon atoms; each $R^{32}$ is independently selected from —OH and —OC(O)$R^{34}$; $R^{33}$ is —OC(O)$R^{34}$; and each $R^{34}$ is independently selected from a straight or branched chain alkyl or alkenyl group having from about 4 to about 22 carbon atoms; u is an average number of from about 1 to about 10, for example 1.5 or 3; each x is independently from about 0 to about 20 and the total x is from 1 to about 60; when u is greater than 1, total x is a multiple of u; y is a multiple of u with the multiplication factor being an average number of from 0 to about 5, for example 1.5; and z is an average number such that z is approximately equal to u. Preferred are: sucrose, glucose or sorbitan sug units; u=about 1; x=about 1 to about 20 and total x from about 1 to about 60; $R^{31}$ having two carbon atoms; $R^{32}$ being —OH or —OC(O)$R^{34}$; and $R^{34}$ being an alkyl or alkenyl moiety having from about 8 to about 18 carbon atoms; y=about 1 to about 4; and z=u.

One preferred example is depicted below in Structure (XVIII):

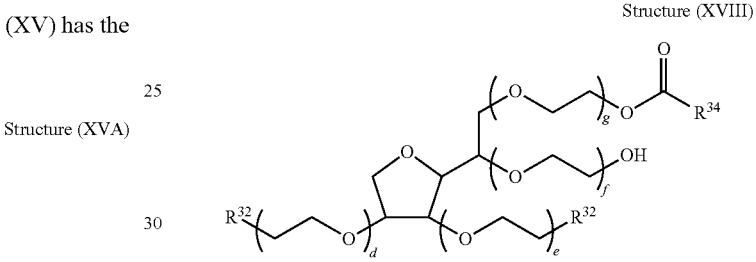

Structure (XVIII)

wherein sug is sorbitan, each $R^{32}$ is —OH, $R^{33}$ is an alkyl or alkenyl having from about 6 to about 20 carbons, and the sum of d, e, f and g is from about 1 to about 50. Examples conforming to formula (5) include polyoxyethylene (20) sorbitan monolaurate (AGNIQUE® SML-20-U; Tween® 20), polyoxyethylene (5) sorbitan monooleate (AGNIQUE® SMO-5), polyoxyethylene (20) sorbitan monooleate (AGNIQUE® SMO-20-U; Tween® 80); and polyoxyethylene (30) sorbitan monooleate (AGNIQUE® SMO-30). Other preferred examples conform to formula (5) wherein sug is sorbitan, each $R^{32}$ is —OC(O)$R^{34}$, $R^{33}$ and $R^{34}$ are each a straight or branched chain alkyl or alkenyl having from about 6 to about 20 carbons, and the sum of d, e, f and g is from about 1 to about 50. Examples include polyoxyethylene (16) sorbitan tristearate (AGNIQUE® STS-16), polyoxyethylene (20) sorbitan tristearate (AGNIQUE® STS-20), polyoxyethylene (20) sorbitan trioleate (Tween® 85; AGNIQUE® STO-2095).

In still other embodiments, the derivatized saccharide surfactant is of Structure (XIX):

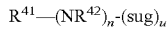 Structure (XIX)

wherein $R^{41}$ is a straight or branched chain substituted or unsubstituted hydrocarbyl selected from alkyl, alkenyl, alkylphenyl, alkenylphenyl having from about 4 to about 22 carbon atoms, $R^{42}$ is hydrogen or $C_{1-4}$ hydrocarbyl, sug is as defined above, n and u are as defined above. An example of a compound of Structure (XIX) is a glucosamine where $R^{41}$ is $C_8H_{17}$ hydrocarbyl, n and u and are about 1, $R^{42}$ is hydrogen, and sug is an open or cyclic glucose. An example is a cyclic glucosamine derivative of the Structure (XIXa):

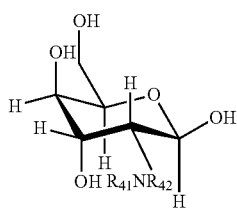

Structure (XIXa)

In other variations of the above embodiments, one or more of the hydroxyl groups present in the derivatized saccharide surfactants are substituted with groups that act to improve characteristics such as solubility and efficacy enhancing capabilities.

For example, the compositions of the invention may comprise silicone functionalized alkyl polyglucoside surfactants, as described in U.S. Pat. No. 6,762,289 B1 to O'Lenick et al. (the contents of which are incorporated herein by reference), wherein from 2 to 5 of the hydroxyl groups present on the sug group in an alkyl polysaccharide surfactant is reacted with an organosiloxane to generate a silicone-functionalized alkyl polysaccharide surfactant exhibiting enhanced water solubility. The silicone-functionalized surfactant is represented by chemical Structure (XX):

$$R^{51}\text{-}(sug)_u(O\text{-organosiloxane})_z \quad \quad \text{Structure (XX)}$$

wherein $R^{51}$ represents a straight or branched chain alkyl or alkenyl having from about 8 to about 22 carbon atoms, sug and u are as defined above, and z is an average number of from about 2 to about 5. Each organosiloxane substituent can contain from 1 to about 1000 silicone atoms, said organosiloxane optionally being further substituted with straight or branched chain alkyl, alkenyl or alkoxy groups.

In some embodiments, the herbicidal composition of the present invention comprises a surfactant component comprising an amine oxide surfactant. In general, amine oxide surfactant comprises an oxyalkylene or a polyoxyalkylene group bonded to the amine oxide nitrogen by a nitrogen-carbon bond wherein the outer terminus of the oxyalkylene or polyoxyalkylene chain is capped with a hydrocarbyl group via an ether linkage.

In some embodiments, amine oxide surfactants of the present invention have a group corresponding to the formula $R^1$—$(XR^2)_m$—$(OR^3)_n$—Z— attached to the amine oxide group via a carbon-nitrogen bond, wherein $R^1$ is a hydrocarbyl group comprising from about 6 to about 22 carbon atoms, $R^2$ and $R^3$ are independently selected from alkylene groups comprising from 2 to 4 carbon atoms, Z is a carbon-nitrogen bond or an oxyhydrocarbylene group comprising from about 2 to about 6 carbon atoms, each X is independently an ether, thioether, sulfoxide, ester, thioester or amide linkage, m is an average number from 0 to about 9, n is an average number from 0 to about 5 and m+n≥1.

In some embodiments, the herbicidal composition comprises an alkyl amine oxide surfactant comprising a hydrophobic moiety and a hydrophilic moiety represented by Structure (XXI):

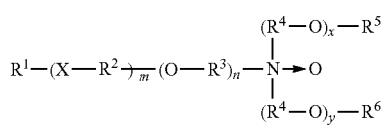

Structure (XXI)

wherein $R^1$ is $C_{1-22}$ a straight or branched chain hydrocarbyl; each X is independently an ether, thioether, sulfoxide, ester, thioester or amide linkage; each $R^2$ is independently $C_{2-6}$ alkylene; each $R^3$ and $R^4$ are independently $C_{2-4}$ alkylene; and $R^5$ and $R^6$ are independently hydrogen, $C_{1-4}$ alkyl or $C_{2-4}$ acyl; x and y are average numbers such that the sum of x and y is from 2 to about 60, more preferably about 2 to about 40, more preferably about 2 to about 20; m is 0 to about 9; and n is 0 to about 5, more preferably about 1 to about 5, still more preferably about 1 to about 3 and when n is not 0 or when m is not 0 and X is an ether, the amine oxide surfactant is termed an etheramine oxide; and m+n is preferably at least one. $R^1$ is preferably a $C_{6-22}$ hydrocarbyl, more preferably a $C_{8-18}$ alkyl, aryl or alkaryl. In some embodiments, m is 0. When m and n are 0, and $R^5$ and $R^6$ are H, $R^1$ is $C_{9-22}$. $R^3$ and $R^4$ are preferably ethyl, n-propyl or i-propyl. In some embodiments, $R^1$ is straight or branched chain $C_{8-18}$ alkyl, aryl or alkaryl, and m is 0. In some other embodiments, $R^1$ is straight or branched chain $C_{8-18}$ alkyl, $R^3$ is ethyl, n-propyl or i-propyl, n is from 1 to about 3, $R^4$ is ethylene, the sum of x and y is from 2 to about 20, and $R^5$ and $R^6$ are hydrogen. In some other embodiments, the surfactant includes commercial surfactants known in the art or referred to herein as "alkyletherdimethylamine oxides" (where n is 1-5, x and y are 0, and $R^5$ and $R^6$ are methyl) and certain "polyoxyalkylene alkyletheramine oxides" (where n is 1-5, x+y is 2 or greater, and $R^5$ and $R^6$ are hydrogen).

A useful class of alkyl amine oxide surfactants are disclosed in U.S. Pat. No. 5,750,468 (the contents of which are incorporated herein by reference for all relevant purposes) to be suitable for preparation of aqueous solution concentrate formulations of various glyphosate salts, the potassium salt being included in the list of salts mentioned. It is disclosed therein that an advantage of the subject surfactants when used in an aqueous composition with glyphosate salts is that these surfactants permit the glyphosate concentration of the composition to be increased to very high levels. The surfactants of U.S. Pat. No. 5,750,468 predominantly comprise one or more surfactants having Structure (XXII):

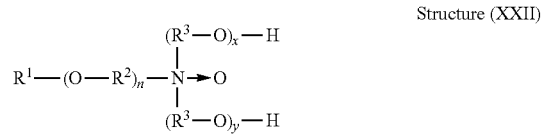

Structure (XXII)

where $R^1$ is straight or branched chain $C_{6-22}$ alkyl, aryl or alkylaryl group; n is an average number from 0 to about 10, more preferably from about 1 to about 10, and when n is not 0 the amine oxide surfactant is termed an etheramine oxide surfactant; $R^2$ in each of the (O—$R^2$)$_n$ groups is independently $C_{1-4}$ alkylene; $R^3$ groups are independently $C_{1-4}$ alkylene; and x and y are average numbers such that x+y is in the range from 2 to about 60. When n is 0, $R^1$ is straight or branched chain $C_{9-22}$ alkyl. An example of an amine oxide of Structure (XXII) is the surfactant from Tomah Products designated AO-14-2 wherein $R^1$ is isodecyl, $R^2$ is n-propyl, $R^3$ is ethyl, n is 1, and x+y is 2.

In reference to Structure (XXII), aryl groups, if present in $R^1$, have 5-7, preferably 6, carbon atoms and may or may not be substituted. The alkyl portion in any alkylaryl group comprising $R^1$ has 1-16 carbon atoms. An example of such an alkylaryl group is alkylphenyl, for example nonylphenyl.

In further reference to Structure (XXII), it is preferred that $R^1$ is a straight or branched chain alkyl group having about 8 to about 18 carbon atoms. The $R^2$ substituent closest to the nitrogen atom (the proximal $R^2$ group) is preferred to be a normal propylene, isopropylene or ethylene group. Where the proximal $R^2$ group is n-propylene, n is preferably 1. Where the proximal $R^2$ group is i-propylene or ethylene, n is preferably in the range of from 1 to 5, more preferably from 2 to 3, and all $R^2$ groups are preferably the same. $R^3$ substituents in preferred examples are independently selected from i-propylene and ethylene, with ethylene more preferred. In some embodiments, x+y is preferred to be in the range of from 2 to 20, from 2 to 10, or even from 2 to 5.

In yet another alternative, the amine oxide surfactants predominantly comprise one or more surfactants having Structure (XXIII):

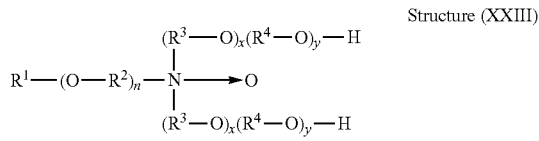

Structure (XXIII)

where $R^1$ is straight or branched chain $C_{6-22}$ alkyl or an aryl or alkylaryl group; n is an average number from 0 to 10, preferably from 1 to about 10 and when n is not 0 the amine oxide surfactant is termed an etheramine oxide surfactant; $R^2$, $R^3$ and $R^4$ are independently $C_{1-4}$ alkylene; and x and y are average numbers such that x+y is in the range from 2 to about 60. When n is 0, $R^1$ is straight or branched chain $C_{9-22}$ alkyl. An example of an amine oxide of formula (XXIII) is the surfactant from Akzo Nobel designated C6602 wherein $R^1$ is $C_{12}$, n is 0, $R^3$ is ethyl, $R^4$ is n-propyl, x=9 and y=2.

In reference to Structure (XXIII), aryl groups, if present in $R^1$, have 5-7, preferably 6, carbon atoms and may or may not be substituted with moieties. The alkyl portion is any alkylaryl group comprising $R^1$ has 1-16 carbon atoms. An example of such an alkylaryl group is alkylphenyl, for example nonylphenyl.

In further reference to Structure (XXIII), it is preferred that $R^1$ is a straight or branched chain alkyl group having about 8 to about 18 carbon atoms, and is derived from the corresponding alcohol. The $R^2$ substituent closest to the nitrogen atom (the proximal $R^2$ group) is preferred to be a normal propylene, isopropylene or ethylene group. Where the proximal $R^2$ group is n-propylene, n is preferably 1. Where the proximal $R^2$ group is i-propylene or ethylene, n is preferably in the range of from 1 to 5, more preferably from 2 to 3, and all $R^2$ groups are preferably the same. $R^3$ and $R^4$ substituents in preferred examples are independently selected from i-propylene and ethylene, with ethylene more preferred. In some embodiments, x+y is preferred to be in the range of from 2 to 20, from 2 to 10, or even from 2 to 5.

In another embodiment, a class of amine oxide surfactants are represented by Structure (XXIV):

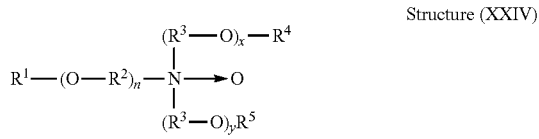

Structure (XXIV)

wherein where $R^1$ is straight or branched chain $C_{6-22}$ alkyl, aryl or alkylaryl group; n is an average number from 0 to about 10 and when n is not 0 the amine oxide is termed an etheramine oxide; $R^2$ and $R^3$ are independently $C_{1-4}$ alkylene; $R^4$ is hydrogen or $C_{1-4}$ alkyl; $R^5$ is $C_{1-4}$ alkyl; and x and y are average numbers such that x+y is in the range from 2 to about 60.

In some embodiments, a class of etheramine oxide surfactants are represented by Structure (XXV):

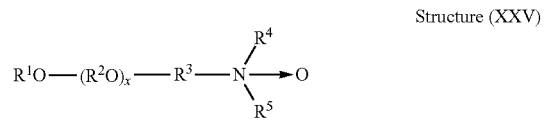

Structure (XXV)

wherein $R^1$ is a hydrocarbyl or substituted hydrocarbyl having from 1 to about 30 carbon atoms; $R^2$ in each of the $(R^{2}O)_x$ groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_y R^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the $(R^2O)_x$ groups is independently $C_2$-$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the $(R^2O)_x$ groups is independently ethylene or propylene, $R^3$ is a linear or branched alkylene or alkenylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the $(R^2O)_x$ groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the $(R^2O)_x$ groups is independently ethylene or propylene, $R^3$ is an ethylene, propylene, or 2-hydroxypropylene group, $R^4$ and $R^5$ are methyl, and x is an average number from about 4 to about 20.

Amidoalkylamine Surfactants

The water-insoluble pesticide component may be dissolved in a surfactant component comprising one or more amidoalkylamine surfactants. The amidoalkylamine surfactants have the general Structure (XXVI):

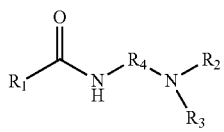 Structure (XXVI)

wherein $R_1$ is a hydrocarbyl or substituted hydrocarbyl having from 1 to about 22 carbon atoms, $R_2$ and $R_3$ are each independently hydrocarbyl or substituted hydrocarbyl having from 1 to about 6 carbon atoms and $R_4$ is hydrocarbylene or substituted hydrocarbylene having from 1 to about 6 carbon atoms.

$R_1$ is preferably an alkyl or substituted alkyl having an average value of carbon atoms between about 4 to about 20 carbon atoms, preferably an average value between about 4 and about 18 carbon atoms, more preferably an average value from about 4 to about 12 carbon atoms, more preferably an average value from about 5 to about 12 carbon atoms, even more preferably an average value from about 6 to about 12 carbon atoms, and still more preferably an average value from about 6 to about 10 carbon atoms. The $R_1$ alkyl group may be derived from a variety of sources that provide alkyl groups having from about 4 to about 18 carbon atoms, for example, the source may be butyric acid, valeric acid, caprylic acid, capric acid, coco (comprising mainly lauric acid), myristic acid (from, e.g., palm oil), soy (comprising mainly linoleic acid, oleic acid, and palmitic acid), or tallow (comprising mainly palmitic acid, oleic acid, and stearic acid). In some embodiments, the amidoalkylamine surfactant component may comprise a blend of amidoalkylamines having alkyl chains of various lengths from about 5 carbon atoms to about 12 carbon atoms. For example, depending upon the source of the $R_1$ alkyl group, an amidoalkylamine surfactant component may comprise a blend of surfactants having $R_1$ groups that are 5 carbon atoms in length, 6 carbon atoms in length, 7 carbon atoms in length, 8 carbon atoms in length, 9 carbon atoms in length, 10 carbon atoms in length, 11 carbon atoms in length, and 12 carbon atoms in length, longer carbon chains, and combinations thereof. In other embodiments, the amidoalkylamine surfactant component may comprise a blend of surfactants having $R_1$ groups that are 5 carbon atoms in length, 6 carbon atoms in length, 7 carbon atoms in length, and 8 carbon atoms in length. In some alternative embodiments, the amidoalkylamine surfactant component may comprise a blend of surfactants having $R_1$ groups that are 6 carbon atoms in length, 7 carbon atoms in length, 8 carbon atoms in length, 9 carbon atoms in length, and 10 carbon atoms in length. In other embodiments, the amidoalkylamine surfactant component may comprise a blend of surfactants having $R_1$ groups that are 8 carbon atoms in length, 9 carbon atoms in length, 10 carbon atoms in length, 11 carbon atoms in length, and 12 carbon atoms in length.

$R_2$ and $R_3$ are independently preferably an alkyl or substituted alkyl having from 1 to about 4 carbon atoms. $R_2$ and $R_3$ are most preferably independently an alkyl having from 1 to about 4 carbon atoms, and most preferably methyl. $R_4$ is preferably an alkylene or substituted alkylene having from 1 to about 4 carbon atoms. $R_4$ is most preferably an alkylene having from 1 to about 4 carbon atoms, and most preferably n-propylene.

In one preferred amidoalkylamine surfactant, $R_1$ is $C_{6-10}$, i.e., an alkyl group having 6 carbon atoms, 7 carbon atoms, 8 carbon atoms, 9 carbon atoms, 10 carbon atoms, or a blend of any of these, i.e., from about 6 carbon atoms to about 10 carbon atoms; $R_2$ and $R_3$ are each methyl; and $R_4$ is n-propylene (i.e., $C_{6-10}$ amidopropyl dimethylamine).

When $R_{124}$ is n-propylene, the amidoalkylamine surfactants are termed amidopropylamine (APA) surfactants. Examples of APA surfactants include Armeen APA 2 (where $R_{121}$ is $C_2$ and $R_{122}$ and $R_{123}$ are each hydrogen), Armeen APA 6 (where $R_{121}$ is $C_6$ and $R_{122}$ and $R_{123}$ are each methyl), Armeen APA 8, 10 (where $R_{121}$ is $C_{8-10}$ and $R_{122}$ and $R_{123}$ are each methyl), Armeen APA 12 (where $R_{121}$ is $C_{12}$ and $R_{122}$ and $R_{123}$ are each methyl), ACAR 7051 (where $R_{121}$ is $C_{5-9}$ and $R_{122}$ and $R_{123}$ are each methyl), ACAR 7059 (where $R_{121}$ is 2-ethyl hexyl and $R_{122}$ and $R_{123}$ are each methyl) and Adsee C80W (where $R_{121}$ is Coco and $R_{122}$ and $R_{123}$ are each methyl).

Alkoxylated Alcohol Surfactants

In some embodiments, the herbicidal compositions of the present invention comprise a surfactant component comprising an alkoxylated alcohol surfactant.

Alkoxylated alcohol co-surfactants of the present invention may have the general Structure (XXVII):

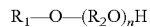 Structure (XXVII)

$R_1$—O—$(R_2O)_n$H wherein $R_1$ is a hydrocarbyl or substituted hydrocarbyl having from about 4 to about 22 carbon atoms; $R_2$ is a hydrocarbylene having 2, 3, or 4 carbon atoms (e.g., ethylene, propylene or isopropylene); and n is an average value ranging from about 2 to about 50.

$R_1$ is preferably an alkyl group having from about 4 to about 22 carbon atoms, more preferably from about 8 to about 18 carbon atoms, and still more preferably from about 12 to about 18 carbons atoms. $R_1$ may be branched or linear. Preferably, $R_1$ is linear. The $R_1$ alkyl group may be derived from a variety of sources that provide alkyl groups having from about 4 to about 22 carbon atoms, for example, the source may be butyric acid, valeric acid, caprylic acid, capric acid, coco (comprising mainly lauric acid), myristic acid (from, e.g., palm oil), soy (comprising mainly linoleic acid, oleic acid, and palmitic acid), or tallow (comprising mainly palmitic acid, oleic acid, and stearic acid). Sources of the $R_1$ group include, for example, coco or tallow, or $R_1$ may be derived from synthetic hydrocarbyls, such as decyl, dodedecyl, tridecyl, tetradecyl, hexadecyl, or octadecyl groups. The $R_1$ alkyl chain in a population of alkoxylated alcohol co-surfactants typically comprises alkyl chains having varying length, for example, from 12 to 16 carbons in length, or from 16 to 18 carbons in length, on average. Most preferably, the $R_1$ alkyl chain comprises predominantly 12 to 16 carbon atoms. $R_2$ is preferably ethylene. The value of n is preferably an average between about 2 and about 30, more preferably between about 2 and about 20, even more preferably between about 2 and about 10.

Specific alkoxylated alcohol surfactants for use in the herbicidal compositions of the present invention include, for example, Ethylans, such as Ethylan 1005, Ethylan 1008, and Ethylan 6830 available from Akzo Nobel; Berols, such as Berol 048, Berol 050, Berol 175, Berol 185, Berol 260, Berol 266, and Berol 84, among others, also available from Akzo Nobel; Brij 30, 35, 76, 78, 92, 97 or 98 available from ICI Surfactants; Tergitol 15-S-3,15-S-5,15-S-7, 15-S-9,15-S-12, 15-S-15 or 15-S-20 available from Union Carbide; or Surfonic L24-7, L12-8, L-5, L-9, LF-17 or LF-42 available from Huntsman.

Specific phosphate esters of alkoxylated alcohol surfactants for use in the herbicidal composition of the present invention include, for example, EMPHOS CS-121, EMPHOS PS-400, and WITCONATE D-51-29, available from Witco Corp. Other examples are indicated in Table II below for the Phospholan produces (available from Akzo Nobel) wherein the surfactants may comprise a mixture of the monoester and diester forms and wherein $R_{94}$ is not present in the diester as indicated and "prop." refers to proprietary and "NR" refers to not reported. In some embodiments, the phosphate esters of the general monoester structure and the general diester structure are not alkoxylated, i.e., m is 0. Examples of commercial products include Phospholan PS-900 and Phospholan 3EA.

TABLE II

| Tradename | $R_{91}$ | $R_{92}$ | $R_{29}/R_{94}$ | m | mono and di forms |
|---|---|---|---|---|---|
| Phospholan CS-131 | nonyl phenol | $C_2$ | H | 6 | mono & di |
| Phospholan CS-1361 | nonyl phenol | $C_2$ | H | 6 | high mono & di |
| Phospholan CS-141 | nonyl phenol | $C_2$ | H | 10 | mono & di |
| Phospholan CS-147 | nonyl phenol | $C_2$ | H | 8 | mono & di |
| Phospholan KPE4 | prop. | prop. | prop. | prop. | mono |
| Phospholan PS-131 | tridecyl | $C_2$ | H | NR | NR |
| Phospholan PS-220 | decyl/tetradecyl | $C_2$ | H | 30 | mono & di |
| Phospholan PS-222 | dodecyl/pentadecyl | $C_2$ | H | 3 | mono & di |
| Phospholan PS-236 | decyl/dodecyl | $C_2$ | H | 7 | mono & di |
| Phospholan PS-900 | tridecyl alcohol | — | H | — | mono & di |
| Phospholan TS-230 | phenyl | $C_2$ | H | 7 | mono & di |
| Phospholan 3EA | triethanolamine amine | — | H | — | mono |

Anionic Surfactants

Anionic surfactants useful as components of the stabilizing system of compositions of the include, without restriction, $C_{8-20}$ alkyl carboxylates including fatty acids, $C_{8-20}$ alcohol sulfates, phosphate esters of alkoxylated tertiary amines, phosphate esters of alkoxylated etheramines, phosphate esters of alkoxylated alcohols such as $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, $C_{8-20}$ alkyl polyoxyethylene sulfosuccinates and sulfosuccinamates, and $C_{8-20}$ acyl glutamates, sarcosinates, isethionates and taurates.

Phosphate Esters of Alkoxylated Tertiary Amines/Etheramines

In some embodiments, the herbicidal composition of the present invention comprises a surfactant component comprising a surfactant selected from among phosphate esters of alkoxylated tertiary amine surfactants or phosphate esters of alkoxylated etheramine surfactants.

Phosphate esters of alkoxylated tertiary amine co-surfactants for use in the herbicidal compositions of the present invention have the general Structures (XXVIIIa) and (XXVIIIb):

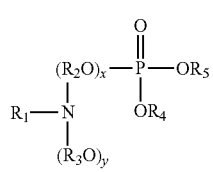

Structure (XXVIIIa)

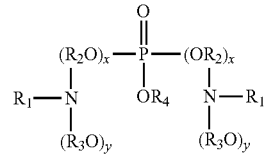

Structure (XXVIIIb)

wherein each $R_1$ is independently a hydrocarbyl or substituted hydrocarbyl having from about 4 to about 22 carbon atoms, $R_2$ and R3 are each independently hydrocarbylene having 2, 3, or 4 carbon atoms (e.g., ethylene, propylene or isopropylene), the sum of each x and y group is an average value ranging from about 2 to about 60, and $R_4$ and $R_5$ are each independently hydrogen or a linear or branched chain hydrocarbyl or substituted hydrocarbyl having from 1 to about 6 carbon atoms.

Each $R_1$ is preferably independently an alkyl having from about 4 to about 22 carbon atoms, more preferably from about 8 to about 18 carbon atoms, and still more preferably from about 12 to about 18 carbons atoms, for example coco or tallow. $R_1$ is most preferably tallow. Each $R_2$ and $R_3$ is preferably ethylene. The sum of each x and y group is preferably independently an average value ranging from about 2 to about 22, more preferably between about 10 and about 20, for example, about 15. More preferably $R_4$ and $R_5$ are each independently hydrogen or a linear or branched chain alkyl having from 1 to about 6 carbon atoms. $R_4$ and $R_5$ are preferably hydrogen.

Specific phosphate esters of alkoxylated tertiary amine surfactants for use in the herbicidal composition of the present invention are described in U.S. 2002/0160918, by Lewis et al. (Huntsman Petrochemical Corporation), such as phosphate esters of tallow amine ethoxylates, including phosphate esters of SURFONIC® T5, phosphate esters of SURFONIC® T15, phosphate esters of SURFONIC® T20, and mixtures thereof, all available from Huntsman International LLC.

Phosphate esters of alkoxylated etheramine co-surfactants for use in the herbicidal compositions of the present invention have the general Structures (XXIXa) and (XXIXb):

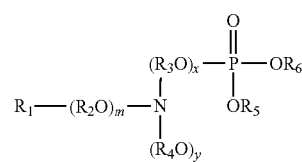

Structure (XXIXa)

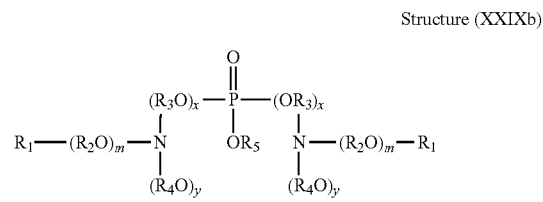

Structure (XXIXb)

wherein each $R_1$ is independently a hydrocarbyl or substituted hydrocarbyl having from about 4 to about 22 carbon atoms; each $R_2$, $R_3$ and $R_4$ is independently a hydrocarbylene having 2, 3, or 4 carbon atoms (e.g., ethylene, propylene or isopropylene); each m is independently an average number from about 1 to about 10; the sum of each x and y group is independently an average value ranging from about 2 to about 60; and each $R_5$ and $R_6$ are independently hydrogen or a linear or branched chain alkyl having from 1 to about 6 carbon atoms.

Each $R_1$ is preferably independently an alkyl having from about 4 to about 22 carbon atoms, more preferably from about 8 to about 18 carbon atoms, from about 10 to about 16 carbon atoms, from about 12 to about 18 carbons atoms, or from about 12 to about 14 carbon atoms. Sources of the $R_1$ group include, for example, coco or tallow, or $R_1$ may be derived from synthetic hydrocarbyls, such as decyl, dodedecyl, tridecyl, tetradecyl, hexadecyl, or octadecyl groups. Each $R_2$ may independently be propylene, isopropylene, or ethylene, and each m is preferably independently from about 1 to 5, such as 2 to 3. Each $R_3$ and $R_4$ may independently be ethylene, propylene, isopropylene, and are preferably ethylene. The sum of each x and y group is preferably independently an average value ranging from about 2 to about 22, such as from about 2 to 10, or about 2 to 5. In some embodiments, the sum of each x and y group is preferably independently between about 10 and about 20, for example, about 15. More preferably $R_5$ and $R_6$ are each independently hydrogen or a linear or branched chain alkyl having from 1 to about 6 carbon atoms. $R_5$ and $R_6$ are preferably hydrogen.

Phosphate esters of alkoxylated alcohol co-surfactants for use in the herbicidal compositions of the present invention have the general Structures (XXXa) and (XXXb):

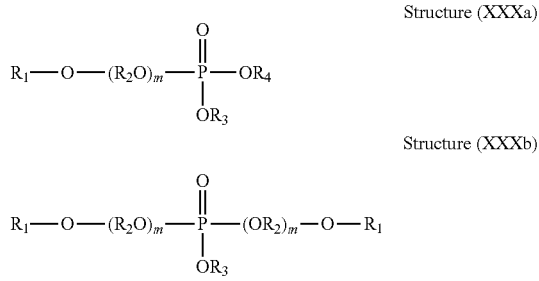

Structure (XXXa)

Structure (XXXb)

wherein each $R_1$ is independently a hydrocarbyl or substituted hydrocarbyl having from about 4 to about 22 carbon atoms; each $R_2$ is independently a hydrocarbylene having 2, 3, or 4 carbon atoms (e.g., ethylene, propylene or isopropylene); each m is independently an average number from about 1 to about 60; and $R_3$ and $R_4$ are each independently hydrogen or a linear or branched chain alkyl having from 1 to about 6 carbon atoms.

Each $R_1$ is preferably independently an alkyl having from about 4 to about 22 carbon atoms, more preferably from about 8 to about 20 carbon atoms, or an alkylphenyl having from about 4 to about 22 carbon atoms, more preferably from about 8 to about 20 carbon atoms. Sources of the $R_1$ group include, for example, coco or tallow, or $R_1$ may be derived from synthetic hydrocarbyls, such as decyl, dodedecyl, tridecyl, tetradecyl, hexadecyl, or octadecyl groups. Each $R_2$ may independently be propylene, isopropylene, or ethylene, and is preferably ethylene. Each m is preferably independently from about 9 to about 15. More preferably $R_3$ and $R_4$ are each independently hydrogen or a linear or branched chain alkyl having from 1 to about 6 carbon atoms. $R_4$ and $R_5$ are preferably hydrogen.

Specific phosphate esters of alkoxylated alcohol surfactants for use in the herbicidal composition of the present invention include, for example, EMPHOS CS-121, EMPHOS PS-400, and WITCONATE D-51-29, available from Akzo Nobel.

Alkoxylated Alcohols

Alkoxylated alcohol surfactants for use in the herbicidal compositions of the present invention have the general Structure (XXXI):

Structure XXXI wherein $R_{111}$ is hydrocarbyl or substituted hydrocarbyl having from 1 to about 30 carbon atoms, $R_{112}$ in each of the $(R_{112}O)_x$ groups is independently $C_2$-$C_4$ alkylene, $R_{113}$ is hydrogen, or a linear or branched alkyl group having from 1 to about 4 carbon atoms, and x is an average number from 1 to about 60. In this context, preferred $R_{111}$ hydrocarbyl groups are linear or branched alkyl, linear or branched alkenyl, linear or branched alkynyl, aryl, or aralkyl groups. Preferably, $R_{111}$ is a linear or branched alkyl or linear or branched alkenyl group having from about 8 to about 30 carbon atoms, $R_{112}$ in each of the $(R_{112}O)_x$ groups is independently $C_2$-$C_4$ alkylene, $R_{113}$ is hydrogen, methyl or ethyl, and x is an average number from about 5 to about 50. More preferably, $R_{111}$ is a linear or branched alkyl group having from about 8 to about 25 carbon atoms, $R_{112}$ in each of the $(R_{112}O)_x$ groups is independently ethylene or propylene, $R_{113}$ is hydrogen or methyl, and x is an average number from about 8 to about 40. Even more preferably, $R_{111}$ is a linear or branched alkyl group having from about 12 to about 22 carbon atoms, $R_{112}$ in each of the $(R_{112}O)_x$ groups is independently ethylene or propylene, $R_{113}$ is hydrogen or methyl, and x is an average number from about 8 to about 30. Preferred commercially available alkoxylated alcohols include: Emulgin™ L, Procol™ LA-15 (from Protameen); Brij™ 35, Brij™ 56, Brij™ 76, Brij™ 78, Brij™ 97, Brij™ 98 and Tergitol™ XD (from Sigma Chemical Co.); Neodol™ 25-12 and Neodol™ 45-13 (from Shell); Hetoxol™ CA-10, Hetoxol™ CA-20, Hetoxol™ CS-9, Hetoxol™ CS-15, Hetoxol™ CS-20, Hetoxol™ CS-25, Hetoxol™ CS-30, Plurafac™ A38 and Plurafac™ LF700 (from BASF); ST-8303 (from Cognis); Arosurf™ 66 E10 and Arosurf™ 66E20 (from Witco/Crompton); ethoxylated (9.4 EO) tallow, propoxylated (4.4 EO) tallow and alkoxylated (5-16 EO and 2-5 PO) tallow (from Witco/Crompton). Also preferred are; SURFONIC™ NP95 of Huntsman (a polyoxyethylene (9.5) nonylphenol); TERGITOL series from Dow and commercially available from Sigma-Aldrich Co. (Saint Louis, Mo.), including TERGITOL-15-S-5, TERGITOL-15-S-9, TERGITOL-15-S-12 and TERGITOL-15-S-15 (made from secondary, linear $C_{11}$ to $C_{15}$ alcohols with an average of 5 moles, 9 moles, 12.3 moles and 15.5 moles of ethoxylation, respectively); the SURFONIC LF-X series from Huntsman Chemical Co. (Salt Lake City, Utah), including L12-7 and L12-8 (made from linear $C_{10}$ to $C_{12}$ alcohols with an average of 7 moles and 8 moles, respectively, of ethoxylation), L24-7, L24-9 and L24-12 (made from linear $C_{12}$ to $C_{14}$ alcohols with an average of 7 moles, 9 moles and 12 moles of ethoxylation, respectively), L68-20 (made from primary, linear $C_{16-18}$ alcohols with an average of 20 moles of ethoxylation) and L26-6.5 (made from linear $C_{12}$ to $C_{16}$ alcohols with an average of 6.5 moles of ethoxylation); and Ethylan 68-30 ($C_{16-18}$ with an average of 20 moles of ethoxylation) available from Akzo Nobel.

Siloxane Surfactants

In some embodiments, the herbicidal composition of the present invention comprises a surfactant component comprising a siloxane surfactant. The siloxane surfactant conforms to formula (XXXII):

Structure (XXXII)

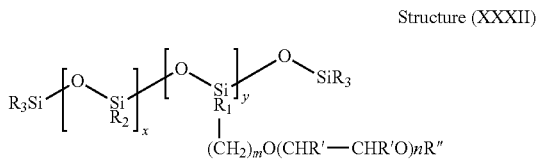

wherein x is an integer or average of integers of 0 to about 100, y is an integer or average of integers of 1 to about 30, each m is independently an integer of 1 to about 20, each n is independently an integer of 1 to about 30, each $R_1$, $R_2$, and $R_3$ group is independently a hydrogen or $C_{1-6}$ hydrocarbyl group, each R' group is independently a hydrogen or $C_{1-4}$ alkyl group, and each R" group is independently a hydrogen $C_{1-20}$ hydrocarbyl or an acyl group. In preferred siloxane surfactants, x is an integer or average of integers of 0 to about 10, more preferably 0 or 1 and most preferably 0. In preferred siloxane surfactants, y is an integer or average of integers of 1 to about 10, most preferably 1. It is preferred that m be an integer of 2 to 6, most preferably 3. It is preferred that n be about 5 to about 20, with all R' groups being hydrogen. It is preferred that $R_1$, $R_2$, and $R_3$ groups be independently selected from hydrogen and $C_{1-4}$ alkyl groups, with hydrogen and methyl groups being particularly preferred. It is preferred that R" is a hydrogen or $C_{1-4}$ alkyl group, with hydrogen and methyl groups again being particularly preferred.

Siloxane surfactants of Structure (XXXII) are generally described in product literature of OSi Specialties, Inc. (e.g., "Silwet® Surfactants," OSi Specialties, Inc., Danbury, Conn., 1994), and in U.S. Pat. No. 3,505,377. Several polyoxyethylene trisiloxanes are available from OSi Specialties as Silwet® surface-active copolymers. Examples suitable as micropore infiltrants for the practice of the present invention include Silwet® L-77, Silwet® 408 and Silwet® 800. Another suitable micropore infiltrant is Sylgard® 309 of Dow Corning.

Alkoxylated Alkylphenols/Dialkylphenols

In some embodiments, the herbicidal composition of the present invention comprises a surfactant component comprising alkoxylated alkylphenols or alkoxylated dialkylphenols having the Structure (XXXIII):

Structure (XXXIII)

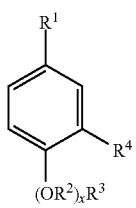

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^{2O}$) groups is independently $C_2$-$C_4$ alkylene, $R^3$ is hydrogen, or a linear or branched alkyl group having from 1 to about 4 carbon atoms, and x is an average number from 1 to about 60. Preferably, $R^1$ and $R^4$ independently linear or branched alkyl groups having from 8 to about 30 carbon atoms, $R^2$ in each of the x ($R^{2O}$) groups is independently $C_2$-$C_4$ alkylene, $R^3$ is hydrogen, methyl, or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

Glyphosate Formulations

Generally, the glyphosate loading of herbicidal compositions of the present invention is at least about 180 g a.e./l, at least about 220 g a.e./l, at least about 260 g a.e./l, at least about 300 g a.e./l, at least about 320 g a.e./l, at least about 360 g a.e./l, at least about 400 g a.e./l, at least about 480 g a.e./l, at least about 500 g a.e./l, at least about 540 g a.e./l, or at least about 600 g a.e./l.

For example, a typical stable liquid glyphosate formulation according to the invention has a concentration of glyphosate in the range of from about 360 to about 600 g a.e./l, preferably from about 450 to about 580 g a.e./l. Generally, these formulations contain glyphosate (a.e.) at a concentration of from about 1 to about 65 wt. % or from about 1 to about 60 wt. %. Typically, these formulations contain glyphosate (a.e.) at a concentration of from about 15 to about 50 wt. % or from about 25 to about 50 wt. %.

Generally, stable liquid glyphosate formulations include one or more alkoxylated mono- and/or diglycerides of the present invention at a concentration of from about 1 to about 25 wt. %, typically from about 1 to about 20 wt. % and, more typically, from 5 to about 15 wt. %.

Generally, the weight ratio of glyphosate (a.e.) to alkoxylated monoglycerides (1-monoglyceride and/or 2-monoglyceride) is from about 1:1 to about 200:1, from about 1:1 to about 100:1, or from about 1:1 to about 50:1. In various embodiments, the weight ratio of these components is from about 1:1 to about 30:1 or from about 1:1 to about 20:1. Typically, the weight ratio of glyphosate (a.e.) to the total proportion of alkoxylated glyceride(s) surfactant of the invention is between about 1:1 and about 30:1 or between about 2:1 and about 25:1 (e.g., typically between about 2.5:1 and about 20:1, between about 1:1 and about 15:1, between about 2:1 and about 10:1, between about 3:1 and about 15:1, or between about 3.5:1 and about 8:1). In various preferred embodiments, the weight ratio of these components is from about 1:1 to about 15:1, more typically from about 1:1 to about 10:1 and, still more typically, from about 1:1 to about 8:1 (e.g., from about 1:1 to about 6:1, or from about 1:1 to about 4:1). In various other preferred embodiments, the weight ratio of glyphosate (a.e.) to total proportion of alkoxylated glyceride(s) is from about 3:1 to about 5:1, or from about 3:1 to about 4:1. In various preferred embodiments, the concentration of glyphosate is in the range of from about 360 to about 600 g a.e./l, and the weight ratio of glyphosate (wt. % a.e.) to the alkoxylated glyceride surfactant is between about 2:1 and about 25:1 (e.g., between about 2.5:1 and about 20:1, or between about 3.5:1 and about 8:1).

Along with the glyphosate salt and alkxoylated glyceride, compositions of the present invention typically include another surfactant such as those detailed elsewhere herein. Generally, any such additional surfactant is present in the composition at a concentration of from about 1 to about 25 wt. % or from about 1 to about 20 wt. % (e.g., from about 1 to about 10 wt. %). Further in accordance with such embodiments the weight ratio of alkoxylated glyceride surfactant to any additional (e.g., second) surfactant is generally from about 0.1:1 to about 10:1 or from about 0.25:1 to about 8:1. Typically, the weight ratio of alkoxylated glyceride to second surfactant is from about 1:1 to about 8:1, more typically from about 1:1 to about 6:1 and, still more typically, from about 1:1 to about 4:1.

In various embodiments, formulations of the present invention may include peaked distribution alkoxylated alkylamine surfactants and/or quaternary alkylammonium salt surfactants as detailed above along with the alkoxylated glycerides of the present invention. Generally in accordance with these embodiments, the weight ratio of glyphosate (wt % a.e.) to total surfactant concentration (e.g., alkoxylated glyceride plus peaked distribution alkoxylated alkylamine) is from about 25:1 to about 0.5:1, from about 20:1 to about 1:1, or from about 8:1 to about 1.5:1.

In accordance with those embodiments in which the formulation comprises an alkoxylated alkyl(ether)amine surfactant (peaked distribution and/or non-peaked distribution) along with one or more alkoxylated glycerides, the weight ratio of glyphosate (a.e.) to the alkoxylated alkyl (ether)amine surfactant(s) is generally from about 25:1 to about 0.5:1, typically from about 20:1 to about 1:1 and, more typically, from about 8:1 to about 1.5:1.

The weight ratio of glyphosate (a.e.) to alkoxylated quaternary alkylammonium salt surfactant(s) is generally from about 25:1 to about 0.5:1, typically from about 20:1 to about 1:1 and, more typically, from about 8:1 to about 1.5:1.

Formulations of the present invention including one or more alkoxylated glyceride surfactants along with one or more other optional surfactants also typically include various other conventional components such as, for example, anti-foaming agents and dyes. These components generally individually or in combination comprise from about 0.1 to about 5 wt. % or from about 0.1 to about 2 wt. % of the formulation. The balance of these formulations is water.

Various other embodiments of the present invention are directed to solid (i.e., dry) herbicidal formulations comprising glyphosate or a salt thereof, optionally along with one or more other active ingredients. These other active ingredients include those generally known in the art including, for example, coherbicides, fungicides, and plant health agents such as those listed elsewhere herein. The preferred salts of glyphosate in this solid formulation are ammonium and sodium. Generally, glyphosate (a.e.) is present in these formulations at a concentration of from about 20 to about 90 wt. % or from about 20 to about 80 wt. %. In various embodiments, glyphosate comprises from about 50 to about 75 wt. % of the formulation. In various other embodiments (e.g., formulations including a second active agent), glyphosate typically comprises from about 20 about 50 wt. % and, more typically, from about 35 to about 50 wt. %. Generally, any second active agent comprises from about 5 to about 90 wt. % or from about 5 to about 50 wt. % of the composition. Typically, the second active agent comprises from about 5 to about 35 wt. % and, still more typically, from about 10 to about 30 wt. % of the composition. Further in accordance with those embodiments including glyphosate and a second active agent, the weight ratio of glyphosate to second active agent generally is from about 1:1 to about 10:1, from about 1:1 to about 6:1, or from about 2:1 to about 6:1.

Generally in accordance with dry compositions of the present invention, the alkoxylated mono- and/or diglyceride comprises up to about 50 wt. % of the composition. Typically in accordance with such embodiments, the alkoxylated mono- and/or diglyceride comprises from about 5 to about 40 wt. % and, more typically, from about 5 to about 35 wt. % or from about 5 to about 25 wt. % of the composition.

Along with the glyphosate salt and alkxoylated glyceride these compositions typically include another surfactant such as those detailed elsewhere herein. Generally, any such additional surfactant is present in the composition at a concentration of from about 1 to about 25 wt. % or from about 1 to about 20 wt. % (e.g., from about 1 to about 10 wt. %). Additional components (e.g., fillers, binders, antifoaming agents, stabilizers and dyes), alone or in combination, may constitute up to about 65 wt. % of the composition. In various embodiments, one or more of these components comprises from about 5 to about 25 wt. % of the composition.

Generally, the weight ratio of glyphosate to alkoxylated mono- or diglyceride in dry compositions is from about 1:1 to about 15:1 or from about 1:1 to about 10:1. Typically, the weight ratio of glyphosate to alkoxylated mono- or diglyceride is from about 1:1 to about 8:1, from about 1:1 to about 6:1, from about 1:1 to about 4:1, from about 1:1 to about 3:1, or from about 1:1 to about 2:1. Generally, the weight ratio of alkoxylated mono- or diglyceride to any second surfactant is from about 1:1 to about 10:1, typically from about 1:1 to about 5:1 and, more typically, from about 1:1 to about 3:1.

The present invention encompasses not merely formulations of glyphosate, but also relates to other herbicidal compositions comprising at least one co-herbicidal active, and at least one surfactant, wherein said at least one surfactant comprises the surfactants of the invention. An herbicidal composition according to the invention can optionally comprise other additives such as ammonium sulfate, potassium sulfate, potassium chloride, sodium sulfate, urea, glycerol, glycols, polyglycols, or mixtures thereof. The present invention also encompasses herbicidal formulations comprising herbicidal actives other than glyphosate including, for example, atrazine, 2,4-dichlorophenoxyacetic acid (2,4-D), dicamba, glufosinate, and paraquat.

Herbicidal compositions of the present can optionally include one or more of the following: a tallowamine ethoxylate, quick-burn additive, humectant, co-herbicide, other pesticides, fungicides, insecticides, plant health agents, other amine compounds, e.g., dimethylamine, isopropylamine, triethylamine, diethanolamine, dye, pigment, corrosion inhibitor, thickener, dispersing agent, calcium sequestrant, foam-moderating or anti-foaming agents, antifreeze, solubility enhancing component, pour-point depressant, anti-gelling agents, pH modifiers, preservatives, hydrotropes, solvents, process aids, or mixtures thereof. Combinations of glyphosate salts and co-herbicide salts are specifically contemplated by the present invention. Preferably, additives used in glyphosate compositions of the present invention possess sufficient solubility or dispersibility in a concentrated aqueous potassium glyphosate solution at a pH of from about 4 to about 7 to allow desired concentrations to be attained.

Suitable anti-foaming agents include silicone-based compositions. An example of a foam-moderating agent for compositions is SAG-10, available from GE Silicones Corporation (Wilton, Conn.). The amount of foam-moderating agent optionally employed is that which is sufficient to inhibit and/or reduce an amount of foam that may otherwise be formed during the process of preparing and containerizing the formulation and/or use thereof to a desired and satisfactory level. Generally, the concentration of foam-moderating agent is in the range from about 0.001% up to about 0.05% by weight of the composition, and typically from about 0.01% to about 0.03% by weight of the composition, although greater or lesser amounts may be employed.

The compositions of the present invention typically comprise one or more preservatives. Preservatives, when used, include, but are not limited to, biocides such as mildewstats and bacteriostats. Suitable examples include methyl, ethyl and propyl parabens; short chain organic acids (e.g. acetic, lactic and/or glycolic acids); bisguanidine compounds (e.g. Dantagard and/or Glydant); short chain alcohols (e.g. ethanol and/or IPA); 5-chloro-2-methyl-4-isothiazolin-3-one (KATHON GC), 2-methyl-4-isothiazolin-3-one (KATHON ICP), 5-chloro-2-methyl-4-isothiazolin-3-one (KATHON 886), all available from Rohm and Haas Company; 2-bromo-2-nitropropane 1, 3 diol (BRONOPOL), from Boots Company Ltd.; propyl-p-hydroxybenzoate (PROXEL CRL), from ICI PLC; 1,2-Benzisothiazol-3(2H)-one biocide (PROXEL GXL) from Zeneca Specialties Co.; o-phenylphenol, Na+ salt (NIPASOL M) from Nipa Laboratories Ltd.; 1,2-Benzoisothiazolin-3-one (DOWICIDE A) and 1-(3-chloroallyl)-3,5,7-triaza-1-azoniaadamantane chloride (DOWICIL 75), and DOWICIL 150 containing cis-1-(3-chloroallyl)-3,5,7-triaza-1-azoniaadmatane chloride (CAS No. 051229-78-8) from Dow Chemical Co.; quaternary alkyl ammonium chloride in 2-propanol (ARQUAD 2.8-50) from Akzo Nobel; 2,4,4'-trichloro-2-hydroxydiphenylether (IRGASAN DP 200), from Ciba-Geigy A.G; NIPACIDE BIT20DPG containing benzisothiazolinone available from Clariant Corporation (Greensboro, N.C.), LEGEND MK anti-microbial biocide available from Rohm and Haas Co. (Philadelphia, Pa.), sorbic acid, mixtures thereof and the like. Preservatives may be included in the compositions of the invention in the range of from about 0.01% to about 0.2% by weight, preferably about 0.1% by weight of the composition.

Suitable antifreeze agents include ethylene glycol and propylene glycol and generally may be present at a concentration of from about 0.1% to about 10% by weight of the composition (e.g., a ready-to-use, RTU, composition prepared by diluting an aqueous concentrate composition or dissolving a solid composition). Antifreeze agents assist in lowering the freezing point of aqueous solutions and maintaining solubility of the components of the composition such that components do not crystallize or precipitate during cycles of freezing and thawing.

Although the compositions of the present invention generally show good overall stability and viscosity properties without the addition of any further additives, the addition of a solubility-enhancing agent (also commonly referred to as a cloud point enhancer or stabilizer) may significantly improve the properties of the formulations. Solubility-enhancing agents include polymer derivatives of ethylene glycol and propylene glycol (e.g., 200-1200 average molecular weight), glycerol, sugars, mixtures thereof and the like in amounts up to about 10%, preferably from about 0.05 to about 10% by weight, more preferably from about 0.1 to about 1% by weight of an RTU composition.

Suitable dyes include, for example, food-grade dyes, pigment dyes, and caramel.

The herbicidal compositions, i.e., liquid concentrates, solid concentrates, and ready to use formulations may further comprise a co-herbicide. In some preferred embodiments, the herbicidal composition is a tank mixed ready to use formulation further comprising a co-herbicide, the tank mixed ready to use formulation being more stable, i.e., characterized by reduced agglomeration or precipitation of the co-herbicide, than conventional glyphosate formulations.

In various embodiments, the co-herbicides are selected from various types of co-herbicides known in the art including, for example, aryloxyphenoxy-propionates (e.g., clodinafop-propargyl, diclofop-methyl, fenoxaprop-ethyl, fluazifop-butyl, haloxyfop-methyl, propaquizafop, quizalofop-ethyl), cyclohexanediones (e.g., butroxydim, clethodim, cycloxydim, sethoxydim, tralkoxydim), sulfonylureas (e.g., amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron, imazosulfuron, metsulfuron, oxasulfuron, primisulfuron, prosulfuron, pyrazosulfuron-ethyl, rimsulfuron, sulfosulfuron, thifensulfuron, triasulfuron, tribenuron, triflusulfuron), imadazolilines (e.g., imazamox), triazolopyrimidines (e.g., flumetsulam and metosulam), triazines (e.g., ametryn, atrazine, cyanazine, desmetryn, dimethametryn, prometon, prometryn, propazine, simazine, simetryne, terbumeton, terbuthylazine, terbutryn, trietazine), triazinone (e.g., hexazinone, metamitron, and metribuzin), uracils (e.g., lenacil and terbacil), pyridazinones (e.g., chloridazon), phenylcarbamates (e.g., desmedipham and phenmedipham), ureas (e.g., chlorotoluron, dimefuron, diuron, fenuron, flumeturon, isoproturon, isouron, linuron, methabenzthiazuron, metobromuron, metoxuron, monolinuron, neburon, siduron, and tebuthiuron), amides (e.g., propanil and pentanochlor), nitriles (e.g., bromofenoxim), bipyridyliums (e.g., diquat and paraquat), diphenylethers (e.g., bifenox, chlomethoxyfen, fluoroglycofen-ethyl, fomesafen, lactofen, and oxyfluorfen), phenylpyrazoles (e.g., pyraflufen-ethyl), N-phenylphthalimides (e.g., flumiclorac-pentyl), oxadiazoles (e.g., oxadiazon), triazolinones (e.g., azafenidin, carfentrazone-ethyl, and sulfentrazone), oxazolidinediones (e.g., pentoxazone), pyridazinones (e.g., norflurazon), pyridinecarboxamides (e.g., diflufenican), triketones (e.g., mesotrione and sulcotrione), isoxazoles (e.g., isoxaflutole), pyrazoles (e.g., benzofenap, pyrazolynate, and pyrazoxyfen), dinitroanilines (e.g., butralin, dinitramine, ethalfluralin, and pendimethalin), pyridines (e.g., dithiopyr), benzoic acids (e.g., chlorthal-dimethyl), carbamates (e.g., chlorpropham, propham, and carbetamide), chloroacetamides (e.g., acetochlor, alachlor, butachlor, and dimethachlor), nitriles (e.g., dichlobenil and chlorthiamid), benzamides (e.g., isoxaben), triazolocarboxamides (e.g., flupoxam), quinoline carboxylic acids (e.g., quinclorac), dinitrophenols (e.g., dinoterb), thiocarbamates (e.g., butylate, cycloate, dimepiperate, EPTC, esprocarb, molinate, orbencarb, pebulate, prosulfocarb, thiobencarb, tiocarbazil, triallate, and vernolate), phosphorodithioates (e.g., bensulide), benzofurans (e.g., benfuresate and ethofumesate), chlorocarbonic acids (e.g., TCA), phenoxycarboxylicacids (e.g., clomeprop, 2,4-D, 2,4-DB, and MCPA), benzoic acids (e.g., dicamba), quinoline carboxylic acids (e.g., quinclorac), phthalamate semicarbazones (e.g., naptalam), and arylaminopropionic acids (e.g., flamprop-methyl).

In various embodiments, water-soluble co-herbicides can be included in the compositions of the present invention. Water-soluble co-herbicides include acifluorfen, acrolein, amitrole, asulam, benazolin, bentazon, bialaphos, bromacil, bromoxynil, chloramben, chloroacetic acid, clopyralid, 2,4-dichlorophenoxyacetic acid (2,4-D), 4-(2,4-dichlorophenoxy)butanoic acid (2,4-DB), dalapon, dicamba, dichlorprop, difenzoquat, diquat, endothall, fenac, fenoxaprop, flamprop, flumiclorac, fluoroglycofen, flupropanate, fomesafen, fosamine, glufosinate, imazameth, imazamethabenz, imazamox, imazapic, imazapyr, imazaquin, imazethapyr, ioxynil, 4-chloro-2-methylphenoxyacetic acid (MCPA), 4-(4-chloro-2-methylphenoxy)butanoic acid (MCPB), mecoprop, methylarsonic acid, naptalam, nonanoic acid, paraquat, picloram, quinclorac, sulfamic acid, 2,3,6-trichlorobenzoic acid (2,3,6-TBA), trichloroacetate (TCA), triclopyr and water-soluble salts thereof.

In various other embodiments, co-herbicides that are less water-soluble can be incorporated into an aqueous herbicidal composition of the present invention. Inclusion of such a co-herbicide is often accompanied by a sufficient quantity of an appropriate surfactant in addition to the alkoxylated glyceride surfactant. In addition, the compositions of the present invention may include finely-divided, water-insoluble herbicides. Examples of herbicides having limited water solubility include, for example, acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, ethyl N,N-dipropylcarbamothioate (EPTC), esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluoroxypyr-1-methylheptyl, flurtamone, fluthiacet-methyl, fomesafen, halosulfuron, haloxyfop-methyl, hexazinone, imazamox, imazosulfuron, indanofan, isoproturon, isouron, isoxaben, isoxaflutole, isoxapyrifop, lactofen, lenacil, linuron, mefenacet, mesotrione, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron, and vernolate. In various preferred embodiments, the co-herbicide is selected from the group consisting of diuron, fluometuron, prometryn, and combinations thereof.

In accordance with those embodiments in which the herbicidally active compound is not a sulfonylurea compound, typically the co-herbicide selected from the group consisting of acifluorfen, acrolein, amitrole, asulam, benazolin, bentazon, bialaphos, bromacil, bromoxynil, chloramben, chloroacetic acid, clopyralid, 2,4-dichlorophenoxyacetic acid (2,4-D), 4-(2,4-dichlorophenoxy)butanoic acid (2,4-DB), dalapon, dicamba, dichlorprop, difenzoquat, diquat, endothall, fenac, fenoxaprop, flamprop, flumiclorac, fluoroglycofen, flupropanate, fomesafen, fosamine, glufosinate, imazameth, imazamethabenz, imazamox, imazapic, imazapyr, imazaquin, imazethapyr, ioxynil, 4-chloro-2-methylphenoxyacetic acid (MCPA), 4-(4-chloro-2-methylphenoxy)butanoic acid (MCPB), mecoprop, methylarsonic acid, naptalam, nonanoic acid, paraquat, picloram, quinclorac, sulfamic acid, 2,3,6-trichlorobenzoic acid (2,3,6-TBA), trichloroacetate (TCA), triclopyr, acetochlor, aclonifen, alachlor, ametryn, anilofos, atrazine, azafenidin, benfluralin, benfuresate, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlornitrofen, chlorotoluron, chlorpropham, chlorthal-dimethyl, chlorthiamid, cinmethylin, clethodim, clodinafop-propargyl, clomazone, clomeprop, cloransulam-methyl, cyanazine, cycloate, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, ethyl N,N-dipropylcarbamothioate (EPTC), esprocarb, ethalfluralin, ethofumesate, etobenzanid, fenoxaprop-ethyl, fenuron, flamprop-methyl, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluoroxypyr-1-methylheptyl, flurtamone, fluthiacet-methyl, fomesafen, haloxyfop-methyl, hexazinone, imazamox, indanofan, isoproturon, isouron, isoxaben, isoxaflutole, isoxapyrifop, lactofen, lenacil, linuron, mefenacet, mesotrione, metamitron, metazachlor, methabenzthiazuron, methyldymron, metobenzuron, metobromuron, metolachlor, metosulam, metoxuron, metribuzin, molinate, monolinuron, naproanilide, napropamide, naptalam, neburon, norflurazon, orbencarb, oryzalin, oxadiargyl, oxadiazon, oxyfluorfen, pebulate, pendimethalin, pentanochlor, pentoxazone, phenmedipham, piperophos, pretilachlor, prodiamine, prometon, prometryn, propachlor, propanil, propaquizafop, propazine, propham, propisochlor, propyzamide, prosulfocarb, pyraflufen-ethyl, pyrazolynate, pyrazoxyfen, pyributicarb, pyridate, pyriminobac-methyl, quinclorac, quinmerac, quizalofop-ethyl, sethoxydim, siduron, simazine, simetryn, sulcotrione, sulfentrazone, tebutam, tebuthiuron, terbacil, terbumeton, terbuthylazine, terbutryn, thenylchlor, thiazopyr, thiobencarb, tiocarbazil, tralkoxydim, triallate, trietazine, trifluralin, triflusulfuron, vernolate, and salts and combinations thereof.

Further in accordance with the present invention, the formulation may comprise a co-herbicide selected from the group consisting of 4-chlorophenoxyacetic acid (4-CPA) or a salt thereof, 2,4-dichlorophenoxyacetic acid (2,4-D) or a salt thereof, 3,4-dichlorophenoxyacetic acid (3,4-DA) or a salt thereof, 4-chloro-2-methylphenoxyacetic acid (MCPA) or a salt thereof, 2,4,5-trichlorophenoxyacetic acid (2,4,5-T) or a salt thereof, 2-(3-chlorophenoxy)propanoic acid (cloprop) or a salt thereof, 2-(4-chlorophenoxy)propanoic acid (4-CPP) or a salt thereof, 2-(2,4-dichlorophenoxy)propanoic acid (dichlorprop) or a salt thereof, 2-(3,4-dichlorophenoxy)propanoic acid (3,4-DP) or a salt thereof, 2-(2,4,5-trichlorophenoxy)propanoic acid (fenoprop) or a salt thereof, 2-(4-chloro-2-methylphenoxy)propanoic acid (mecoprop) or a salt thereof, 4-(4-chlorophenoxy)butanoic acid (4-CPB) or a salt thereof, 4-(2,4-dichlorophenoxy)butanoic acid (2,4-DB)

or a salt thereof, 4-(3,4-dichlorophenoxy)butanoic acid (3,4-DB) or a salt thereof, 4-(4-chloro-2-methylphenoxy)butanoic acid (MCPB) or a salt thereof, 4-(2,4,5-trichlorophenoxy)butanoic acid (2,4,5-TB) or a salt thereof, 3-amino-2,5-dichlorobenzoic acid (chloramben) or a salt thereof, 3,6-dichloro-2-methoxybenzoic acid (dicamba) or a salt thereof, 2,3,6-trichlorobenzoic acid (2,3,6-TBA) or a salt thereof, 2,3,5-trichloro-6-methoxybenzoic acid (tricamba) or a salt thereof, 4-amino-3,6-dichloro-2-pyridinecarboxylic acid (aminopyralid) or a salt thereof, 3,6-dichloro-2-pyridinecarboxylic acid (clopyralid) or a salt thereof, 4-amino-3,5,6-trichloro-2-pyridinecarboxylic acid (picloram) or a salt thereof, 3,5,6-trichloro-2-pyridinyl-oxyacetic acid (triclopyr) or a salt thereof, and combinations thereof.

Regardless of the particular co-herbicide, or combination of co-herbicides present in the formulation, the concentration of one or more co-herbicides in an application mixture is typically from about 0.25 to about 1.0 wt % and, more typically, from about 0.5 to about 1.0 wt %. Additionally or alternatively, the weight ratio of glyphosate (a.e.) to one or more co-herbicides is typically from about 0.5 to about 4.0 and, still more typically, from about 1.0 to about 2.0.

Water-insoluble fungicides that may be included in the formulations of the present invention include, for example, those defined by the genera triazoles, strobilurins, acylamino acids, pyrimidines, pyridines, arylphenyl ketones, amides, benzanilides, imidazoles, dinitrophenols, morpholines, phenylsulfamides amd organophosphorus fungicides. Examples include benalaxyl, benlaxyl-M, bromuconazole, bupirimate, cyflufenamid, difenoconazole, dinobuton, dodemorph, dodemorph acetate, fenoxanil, flusilazole, flutolanil, imazalil, imibenconazole, ipconazole, isoprothiolane, kresoxim-methyl, mandipropamid, mepronil, metconazole, metrafenone, penconazole, picoxystrobin, prochloraz, pyraclostrobin, pyrazophos, silthiofam, tebuconazole, tolclofos-methyl, tolylfluanid, triadimefon, and trifloxystrobin. Suitable water-insoluble fungicides include benalaxyl, benlaxyl-M, dodemorph acetate, flutolanil, ipconazole, kresoxim-methyl, metconazole, picoxystrobin, pyraclostrobin, and tebuconazole.

Water-insoluble insecticides that may be included in formulations of the present invention include, for example, those defined by the genera organophosphorus, insect growth regulators (such as chitin synthesis inhibitors, juvenile hormone mimics, and moulting hormones, inhibitors and mimics), pyrethroids, phthalimides, pyrazoles, organochlorines, carbamates and nicotinoids. Some preferred insecticides include, but are not limited to, azinphos-ethyl, beta-cypermethrin, coumaphos, fenoxycarb, pyridaphenthion, pyrimidifen, and tetramethrin.

Formulations of the present invention may generally be prepared by mixing the glyphosate salt solution, prepared as outlined above, together with other ingredients in a suitable mixing vessel with agitation, such as a blender. Surfactant concentrations can range from about 2 to about 20 wt. %, in another embodiment, from about 4 to about 10 wt. %.

Various embodiments of the present invention are directed to aqueous concentrate compositions including glyphosate along with one or more alkoxylated glycerides. An herbicidal concentrate of the present invention may be prepared by combining the required amounts of glyphosate, water, surfactant, etc., with mixing using a mechanical stirrer or any other suitable container or device producing the necessary amount of agitation or circulation to thoroughly mix the ingredients. The order of addition of the starting materials is not narrowly critical to the stability of the final concentrate. Generally, an aqueous concentrate may include glyphosate (a.e.) at a concentration of at least about 20 wt. %, typically at least about 25 wt. % and, more typically, at least about 30 wt. %. Further in accordance with these embodiments, alkoxylalted glycerides may be present at concentrations of at least about 1 wt. %, at least about 5 wt. %, or at least about 10 wt. %.

For example, a typical aqueous concentrate according to the invention contains glyphosate acid equivalent in the range of from about 20 to about 50 wt. %, from about 30 to about 45 wt. %, or from about 35 to about 40 wt. %. In accordance with these and various other advantageous embodiments, aqueous concentrates typically contain from about 1.2 to about 22.5 wt. %, from about 5 to about 20 wt. %, or from about 10 to about 15 wt. % total alkoxylated glyceride surfactant. The aqueous concentrates of the invention typically contain at least one alkoxylated monoglyceride (1-monoglyceride and/or 2-monoglyceride) at a concentration of from about 1.5 to about 10 wt. %, or from about 2.5 to about 7.5 wt. %. In these and various other preferred embodiments, aqueous concentrates of the present invention typically contain at least one alkoxylated diglyceride (1,2-diglyceride and/or 1,3-diglyceride) at a concentration of from about 1.5 to about 10 wt. %, or from about 2.5 to about 7.5 wt. %.

For application to a field for control of weeds, a typical formulation according to the invention contains glyphosate acid equivalent in the range of from about 0.1 to 18 wt. %, typically 0.1 to 5 wt. %, more typically 0.2 to 3 wt. %, most commonly 0.5 to 2 wt. %. However, stronger mixtures, e.g., in the range from about 2 to about 15 wt. % surfactant may be desirable for some applications.

A solid concentrate of the present invention may also be prepared by combining the required amounts of glyphosate, surfactant, etc. using a mechanical stirrer, ball milling, or any other suitable container or device producing the necessary amount of agitation or circulation to thoroughly mix the ingredients. The order of addition of the materials to prepare the solid concentrate is not narrowly critical to the stability of the final concentrate. Compositions of the present invention ready for use (i.e., RTU compositions) can be prepared by diluting an aqueous herbicidal concentrate or dissolving a solid concentrate with an appropriate amount of water. The present invention is also directed to a method for killing or controlling weeds or other unwanted plants by spraying or otherwise applying a herbicidally effective amount of the RTU or diluted concentrate formulations described herein to the foliage of the plants to be treated. The herbicidal spray compositions included in the present invention can be applied to the foliage of the plants to be treated through any of the appropriate methods that are well known to those having skill in the art. In some embodiments, the RTU composition is packaged in a portable container suitable for hand carry by the user and fitted with an apparatus for manually releasing the composition from the container onto the foliage of the plants to be treated in the form of a spray.

The compositions of the present invention can be used to kill or control the growth of a wide variety of plants. Particularly important annual dicotyledonous plant species include, without limitation, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portu-* laca spp.), Russian thistle (*Salsola* spp.), *sida* (*Sida* spp.), wild mustard (*Sinapis arvensis*) and cocklebur (*Xanthium* spp.).

Particularly important annual monocotyledonous plant species that may be killed or controlled using the compositions of the present invention include, without limitation, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used include, without limitation, mugwort (*Artemisia* spp.), milkweed (*Asclepias* spp.), Canada thistle (*Cirsium arvense*), field bindweed (*Convolvulus arvensis*) and kudzu (*Pueraria* spp.).

Particularly important perennial monocotyledonous plant species for control of which a composition of the invention can be used include, without limitation, brachiaria (*Brachiaria* spp.), bermudagrass (*Cynodon dactylon*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used include, without limitation, horsetail (*Equisetum* spp.), bracken (*Pteridium aquilinum*), blackberry (*Rubus* spp.) and gorse (*Ulex europaeus*).

Generally, various embodiments of the present invention are directed to methods for controlling unwanted vegetation comprising applying an effective amount of the herbicidal formulation to the unwanted vegetation. The glyphosate formulation of the invention should be applied to plant foliage at an application rate sufficient to give the desired effect. Application rates are usually expressed as amount of glyphosate ae per unit area of land treated, e.g. grams ae per hectare (g a.e./ha). Suitable herbicidally efficacious application or spray rates used in the practice of the present invention will vary depending on the particular composition and concentration of active ingredients, the desired effects, plant species treated, weather and other factors. What constitutes a "desired effect" varies according to the standards and practice of those who investigate, develop, market, and use glyphosate products. For example, the amount of glyphosate a.e. applied per unit area to give, consistently and reliably, at least 85% control of a plant species as measured by growth reduction or mortality is often used to define a commercially effective rate.

Preferred compositions of the invention provide equivalent herbicidal efficacy by comparison with commercial standard formulations of glyphosate. "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present invention, is within the skill of the ordinary agricultural scientist. Those skilled in the art will likewise recognize that individual plant conditions, weather, and growing conditions, as well as the specific formulation selected, will influence the degree of biological effectiveness achieved in practicing this invention. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition of this invention. Depending on the degree of control desired, the age and species of the plants, weather conditions and other factors, typically the glyphosate application rate is an herbicidally effective amount of about 0.1 to about 10 kg a.e./ha and preferably from about 0.25 to about 2.5 kg a.e./ha, although greater or lesser amounts may be applied.

As noted, the formulation may comprise a glyphosate salt selected from the group consisting of ammonium glyphosate, diammonium glyphosate, sodium glyphosate, potassium glyphosate, isopropylammonium glyphosate, and combinations thereof. Other suitable glyphosate salts include the monoethanolamine (MEA), diethanolamine (DEA), triethanolamine (TEA), trimesium (TMS) salts, and combinations thereof.

In various preferred embodiments, aqueous concentrate formulations of the present invention comprise ammonium glyphosate. In various other preferred embodiments, aqueous concentrate formulations of the present invention comprise potassium glyphosate. Typically, aqueous concentrate formulations that are diluted for use have a potassium glyphosate loading of at least 320, at least 400, at least 500, or at least 600 g a.e./L. Potassium glyphosate-containing formulations typically have a viscosity of not greater than about 800 centipoise (cPs), not greater than about 600 cPs, not greater than about 400 cPs, not greater than about 300 cPs, or not greater than about 200 cPs at 10° C. and at 45/s shear rate. Formulation viscosities within these limits are generally preferred for ease of processing of the formulation under standard conditions (e.g., pumping with standard pumping equipment). Additionally or alternatively, potassium glyphosate-containing formulations typically have a density of at least about 1.050, at least about 1.150, at least about 1.250, at least about 1.350, or at least about 1.450 grams/liter.

In still further preferred embodiments, the formulation comprises isopropylammonium glyphosate. The formulation may also comprise a mixture of potassium glyphosate and isopropylammonium glyphosate, including, for example mixtures including potassium glyphosate and isopropylammonium glyphosate in a molar ratio between about 90:10 and about 10:90 (e.g., between about 70:30 and about 30:70).

In various other preferred embodiments, the formulation comprises the monoethanolamine (MEA) salt of glyphosate. Preferably in accordance with such embodiments, the formulations have a loading of MEA glyphosate salt of at least 400, at least about 500, or at least about 600 g a.e./L.

In accordance with foregoing, in accordance with various preferred embodiments the herbicidal formulations are characterized by one or more the following: (i) a mixture of ethoxylated mono- and diglycerides having a mono to di ratio of greater than about 50:50 (wt. ratio); and/or (ii) a glyphosate content of at least about 180 g a.e./l; and/or (iii)

a weight ratio of glyphosate (a.e.) to the sum of alkoxylated mono and diglyceride surfactant of between about 1:1 and about 30:1; and/or (iv) a concentration of glyphosate in the range of from about 360 to about 600 g a.e./l, and the weight ratio of glyphosate (wt % a.e.) to the alkoxylated glyceride surfactant is between about 2:1 and about 25:1.

DEFINITIONS

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "substituted hydrocarbyl" as used herein describes hydrocarbyl moieties that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like. Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like. The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

The term "cyclic" as used herein alone or as part of another group denotes a group having at least one closed ring, and includes alicyclic, aromatic (arene) and heterocyclic groups.

The term "acyl," as used herein alone or as part of another group, denotes the moiety formed by removal of the hydroxyl group from the group —COOH of an organic carboxylic acid, e.g., RC(O)—, wherein R is R1, R1O—, R1R2N—, or R1S—, R1 is hydrocarbyl, heterosubstituted hydrocarbyl, or heterocyclo and R2 is hydrogen, hydrocarbyl or substituted hydrocarbyl.

The present invention will now be illustrated by the following non-limiting examples.

Example 1

The % Control of wheat was obtained over 28 days after treatment by the University of Georgia research facility. Six samples were compared under the same conditions. The glyphosate acid to surfactant blend weight ratio is 2:1 (a.e.). The spray rates employed were 710 and 355 g glyphosate a.e./hectare (ha) in all six samples. Sample #1 contains glyphosate alone as the negative (baseline) control. The second sample contains glyphosate and tallowamine-15EO and it was used as a positive control because tallowamine-15EO is one of the most popular and effective surfactants for glyphosate formulations. The rest of the four samples contained glyphosate and various ethoxylated mono/diglycerides according to the invention.

TABLE 1

Formulation Details for Example 1

| Sample # | Formulation Description |
|---|---|
| 1 | Glyphosate, monoammonium salt (Without surfactant) |
| 2 | Glyphosate, monoammonium salt + FLOMO TD-20A Tallowamine ethoxylate-15EO (70-75% active wt) (available from Akzo Nobel) |
| 3 | Glyphosate, monoammonium salt + REWODERM LI 67-75** PEG-80* glyceryl cocoate (75% active wt) |

TABLE 1-continued

Formulation Details for Example 1

| Sample # | Formulation Description |
|---|---|
| 4 | Glyphosate, monoammonium salt + REWODERM LI 520-70** PEG-200* hydrogenated glyceryl palmate (70% active wt) |
| 5 | Glyphosate, monoammonium salt + REWODERM LI 63** PEG-30* glyceryl cocoate (100%) |
| 6 | Glyphosate, monoammonium salt + REWODERM LI S 80** PEG-200* hydrogenated glyceryl Palmate; PEG-7* glyceryl Cocoate (~90%) |

*Polyethylene glycol including 80, 200, 30, or 7 repeating units, n, in HO—($CH_2CH_2O$)n—
**Available from Evonik It can be seen from the data, all four glyphosate samples containing ethoxylated mono/diglycerides surfactants in accordance with the invention showed improved efficacy compared to the first glyphosate sample without the surfactant. At the rate of 710 g a.e./ha, all four samples containing mono/diglycerides showed similar efficacy to the sample containing tallowamine-15EO. At the rate of 355 g a.e./ha, only the sample containing PEG-80 glyceryl cocoate showed similar efficacy to the sample containing tallowamine-15EO.

Example 2

The % Control of wheat was obtained over 28 days after treatment by the University of Georgia research facility. Six samples were compared under the same conditions. The spray rate shown here was 475 g a.e./ha in all six samples. Sample #1 contains glyphosate alone as the negative control. Sample #2 contains glyphosate and tallowamine-15EO and it was used as a positive control. The rest of the four samples contained glyphosate and various ethoxylated mono/diglycerides in accordance with the invention. Sample 4 had twice as much surfactant as did sample 5.

TABLE 2

Formulation Details for Example 2

| Sample # | Formulation Description | Weight Ratio of Glyphosate (a.e.) to surfactant blend |
|---|---|---|
| 1 | Glyphosate, monoammonium salt | Without surfactant |
| 2 | Glyphosate, monoammonium salt + FLOMO TD-20A Tallowamine ethoxylate-15EO (70-75%) (available from Akzo Nobel) | 2 |
| 3 | Glyphosate, monoammonium salt + ACCONON CO-7 PEG-7** glyceryl cocoate (100%) (available from Abitech) | 3 |
| 4 | Glyphosate, monoammonium salt + REWODERM LI-67-75 PEG-80** glyceryl cocoate (75%) | 2 |
| 5 | Glyphosate, monoammonium salt + REWODERM LI-67-75 PEG-80** glyceryl cocoate (75%) | 4 |
| 6 | Glyphosate, monoammonium salt + ACCONON S-35 PEG-35** glyceryl soyate (100%) (available from Abitech) | 3 |

**Polyethylene glycol including 7, 80, or 35 repeating units, n, in HO—($CH_2CH_2O$)n—

As seen from the data, all four glyphosate samples containing ethoxylated mono/diglycerides surfactant in accordance with the invention demonstrated improved efficacy compared to the first glyphosate sample without surfactant, and all four samples containing mono/diglycerides showed similar efficacy to the sample containing tallowamine-15EO (TD-20A). Samples 4 and 5 had similar efficacy even though sample 4 has twice as much surfactant as did sample 5.

Example 3

Aqueous concentrate compositions are prepared containing potassium glyphosate salt, reported in % by weight, and an alkoxylated glyceride surfactant of the present invention. The alkoxylated glyceride surfactant may be in the form of any mono/diglyceride alkoxylate detailed herein. The compositions may also contain an optional surfactant (Surfactant 2), an optional silicone-based anti-foaming agent, and an optional dye. Table 3 provides the details for compositions including combinations of:
(i) potassium glyphosate;
(ii) alkoxylated glyceride surfactant;
(iii) Surfactant 2;
(iv) anti-foaming agent; and
(v) dye.

Surfactant 2 includes cationic, anionic, nonionic, and amphoteric surfactants well-known to one skilled in the art and/or described elsewhere herein. The anti-foaming agent may include those known in the art including silicone based anti-foaming agents described elsewhere herein. The dye may include those generally known in the art including solution dyes, food grade dyes, pigment dyes, and caramel.

Although this example details formulations including the potassium salt of glyphosate, suitable compositions of the type described above may also be prepared including other glyphosate salts including, for example, sodium, ammonium, diammonium, monoethanolamine, and dimethylamine salts.

TABLE 3

GLYPHOSATE ONLY FORMULATIONS

| | RANGE (Low % w/w to High % w/w) | A | B | C | D | E | F | G |
|---|---|---|---|---|---|---|---|---|
| Wt % Potassium Glyphosate (Technical Grade) | 1 to 65% | 49% | 49% | 27% | 27% | 60% | 2% | 49% |
| Wt % Alkoxylated Glyceride | 0 to 25% | 10% | 5% | 15% | 6% | 4% | 2% | 0% |
| Wt % Surfactant #2 | 0 to 25% | 0% | 5% | 0% | 6% | 0% | 0% | 0% |

TABLE 3-continued

GLYPHOSATE ONLY FORMULATIONS

| | RANGE (Low % w/w to High % w/w) | A | B | C | D | E | F | G |
|---|---|---|---|---|---|---|---|---|
| Wt % Antifoam | 0 to 2% | 0.5% | 0.5% | 0.5% | 0.5% | 0.0% | 0.5% | 0.5% |
| Wt % Dye | 0 to 2% | 0.1% | 0% | 0% | 0% | 0% | 0% | 0% |
| Water | balance | 40% | 41% | 58% | 61% | 36% | 96% | 50% |
| Total | | 100% | 100% | 100% | 100% | 100% | 100% | 100% |

For the alkoxylated glyceride surfactant component, the weight ratio of monoglyceride to diglyceride may be greater than about 50:50 (e.g., from about 60:40 to about 99:1, from about 65:35 to about 95:5, or from about 70:30 to about 90:10). It is to also be understood that the weight ratio of monoglyceride to diglyceride may be less than 50:50 without departing from the scope of the present invention.

Example 4

Aqueous concentrate compositions are prepared containing isopropylammonium (IPA) glyphosate salt, reported in % by weight, and an alkoxylated glyceride surfactant of the present invention in the form of any mono/diglyceride alkoxylate detailed herein. Compositions may also contain an optional surfactant (Surfactant 2) of the types detailed in Example 3 and elsewhere herein, an optional silicone-based anti-foaming agent detailed in Example 3 and elsewhere herein, and/or an optional dye of the types detailed in Example 3 and elsewhere herein.

Example 5

Dry formulations are prepared containing ammonium glyphosate salt, reported in % by weight, and an alkoxylated glyceride surfactant of the present invention. The alkoxylated glyceride surfactant may be in the form of any mono/diglyceride alkoxylate detailed herein. The compositions may also contain an optional surfactant (Surfactant 2), and various other components (e.g., fillers, binders, silicone-based anti-foaming agents, stabilizers, and dyes).

Table 5 provides the details for compositions including combinations of:
(i) ammonium glyphosate;
(ii) alkoxylated glyceride surfactant;
(iii) Surfactant 2;
(iv) filler;
(v) binder;
(vi) anti-foaming agent;
(vii) stabilizer; and
(v) dye.

Surfactant 2, the anti-foaming agent, and dye may include those generally known in the art including those described in Example 3 or elsewhere herein. The filler and binder may be any known in the art as suitable for use in herbicidal formulations.

TABLE 4

GLYPHOSATE ONLY FORMULATIONS

| | RANGE (Low % w/w to High % w/w) | H | I | J | K | L | M | N |
|---|---|---|---|---|---|---|---|---|
| Wt % Isopropylammonium Glyphosate (Technical Grade) | 1 to 60% | 50% | 50% | 41% | 41% | 18% | 2% | 2% |
| Wt % Alkoxylated Glyceride | 0 to 25% | 7% | 12% | 6% | 14% | 6% | 2% | 2% |
| Wt % Surfactant #2 | 0 to 25% | 5% | 0% | 4% | 0% | 6% | 0% | 2% |
| Wt % Antifoam | 0 to 2% | 0.5% | 0.5% | 0.5% | 0.2% | 0.2% | 0.1% | 0.1% |
| Wt % Dye | 0 to 2% | 0.1% | 0.1% | 0.1% | 0.0% | 0.0% | 0.1% | 0.0% |
| Water | balance | 37% | 37% | 48% | 45% | 70% | 96% | 94% |
| Total | | 100% | 100% | 100% | 100% | 100% | 100% | 100% |

For the alkoxylated glyceride surfactant component, the weight ratio of monoglyceride to diglyceride may be greater than about 50:50 (e.g., from about 60:40 to about 99:1, from about 65:35 to about 95:5, or from about 70:30 to about 90:10). It is to also be understood that the weight ratio of monoglyceride to diglyceride may be less than 50:50 without departing from the scope of the present invention.

Although this example details formulations including the ammonium salt of glyphosate, suitable compositions of the type described above may also be prepared including other glyphosate salts including, for example, sodium, potassium, diammonium, monoethanolammonium, and dimethylammonium salts.

TABLE 5

| | RANGE (Low % w/w to High % w/w) | A | B | C | D | E | F | G |
|---|---|---|---|---|---|---|---|---|
| GLYPHOSATE ONLY FORMULATIONS | | | | | | | | |
| Wt % Ammonium Glyphosate (Technical Grade) | 20 TO 90 | 90% | 72% | 68% | 72% | 65% | 20% | 50% |
| Wt % Surfactant #1 | 0 TO 50 | 9% | 27% | 27% | 12% | 12% | 8% | 25% |
| Wt % Surfactant #2 | 0 TO 50 | 0% | 0% | 0% | 10% | 10% | 8% | 0% |
| Wt % Filler | 0 TO 90 | 0% | 0% | 4% | 2% | 12% | 60% | 24% |
| Wt % Binder | 0 TO 50 | 0% | 0% | 0% | 3% | 0% | 3% | 0% |
| Wt % Antifoam | 0 TO 5 | 0% | 0% | 0% | 0% | 0% | 0% | 0% |
| Wt % Stabilizer | 0 TO 10 | 1% | 1% | 1% | 1% | 1% | 1% | 1% |
| Wt % Dye | 0 TO 10 | 0% | 0% | 0% | 0% | 1% | 0% | 0% |
| Total | | 100% | 100% | 100% | 100% | 100% | 100% | 100% |

For the alkoxylated glyceride surfactant component, the weight ratio of monoglyceride to diglyceride may be greater than about 50:50 (e.g., from about 60:40 to about 99:1, from about 65:35 to about 95:5, or from about 70:30 to about 90:10). It is to also be understood that the weight ratio of monoglyceride to diglyceride may be less than 50:50 without departing from the scope of the present invention.

Example 6

Dry formulations are prepared containing ammonium glyphosate salt, reported in % by weight, another active ingredient, and an alkoxylated glyceride surfactant of the present invention. The alkoxylated glyceride surfactant may be in the form of any mono/diglyceride alkoxylate detailed herein.

The additional active ingredient may be in the form of a coherbicide, a fungicide, or a plant health agent known in the art and/or as detailed elsewhere herein.

The compositions may also contain an optional surfactant (Surfactant 2), and various other components (e.g., fillers, binders, silicone-based anti-foaming agents, stabilizers, and dyes) described above in Examples 3 and 5 and elsewhere herein.

We claim:

1. A solid herbicidal formulation comprising at least one herbicidally active compound and a surfactant comprising at least one alkoxylated monoglyceride, at least one alkoxylated diglyceride, or a mixture of alkoxylated mono- and diglycerides, provided the composition does not contain a sulfonylurea compound, and wherein the concentration of alkoxylated glyceride surfactant is from 5 to 40 wt. %.

2. The herbicidal formulation according to claim 1 comprising glyphosate or a salt thereof.

3. The formulation of claim 1 wherein the at least one alkoxylated monoglyceride, at least one alkoxylated diglyceride, or a mixture thereof comprises mono and diglycerides corresponding to the formulae:

TABLE 6

| | RANGE (Low % w/w to High % w/w) | H | I | J | K | L | M | N |
|---|---|---|---|---|---|---|---|---|
| GLYPHOSATE PLUS ONE OR MORE ADDITIONAL ACTIVE INGREDIENT FORMULATIONS | | | | | | | | |
| Wt % Ammonium Glyphosate (Technical Grade) | 20 TO 90 | 50% | 50% | 34% | 50% | 50% | 20% | 40% |
| Wt % 2nd Active Ingredient | 0 TO 90 | 25% | 22% | 34% | 22% | 15% | 5% | 10% |
| Wt % Surfactant #1 | 0 TO 50 | 24% | 27% | 27% | 12% | 12% | 10% | 25% |
| Wt % Surfactant #2 | 0 TO 50 | 0% | 0% | 0% | 10% | 10% | 0% | 0% |
| Wt % Filler | 0 TO 90 | 0% | 0% | 4% | 2% | 12% | 55% | 24% |
| Wt % Binder | 0 TO 50 | 0% | 0% | 0% | 3% | 0% | 9% | 0% |
| Wt % Antifoam | 0 TO 5 | 0% | 0% | 0% | 0% | 0% | 0% | 0% |
| Wt % Stabilizer | 0 TO 10 | 1% | 1% | 1% | 1% | 1% | 1% | 1% |
| Wt % Dye | 0 TO 10 | 0% | 0% | 0% | 0% | 1% | 0% | 0% |
| Total | | 100% | 100% | 100% | 100% | 100% | 100% | 100% |

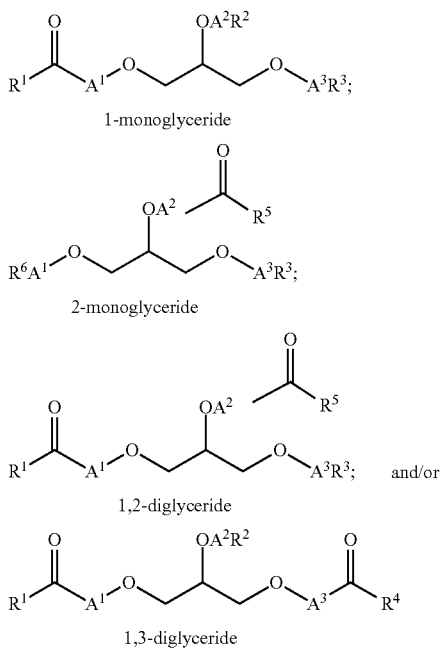

1-monoglyceride 2-monoglyceride 1,2-diglyceride and/or 1,3-diglyceride wherein each of $R^1$, $R^4$ and $R^5$ is independently selected from $C_8$ to $C_{22}$ linear or branched, saturated or unsaturated aliphatic groups; each of $R^2$, $R^3$, and $R^6$ is independently selected from H and a lower alkyl, lower alkenyl, or aryl group; and each of $A^1$, $A^2$ and $A^3$ is independently either a carbon to oxygen bond or an alkylene oxide group oriented to have a terminal O bonded to a C and a terminal C bonded to an O and containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, each of said alkoxylated mono and diglycerides contains a total of from 5 to 200 alkylene oxide units.

4. The formulation of claim 3 wherein each of $A^1$, $A^2$, and $A^3$ is independently an alkylene oxide group containing from 1 to 100 alkylene oxide units.

5. The formulation of claim 3 wherein each of $A^1$, $A^2$, and $A^3$ is independently an alkylene oxide group including alkylene oxide units independently selected from the group consisting of —[OCH$_2$]—, —[OC$_2$H$_4$]—, —[OC$_3$H$_6$]— and —[OC$_4$H$_8$]—.

6. The formulation of claim 3 wherein $A^1$, $A^2$ and $A^3$ are each alkylene oxide groups containing —[OC$_2$H$_4$]— ethylene oxide units.

7. The formulation of claim 3 wherein $R^1$, $R^2$, and $R^3$ are each independently derived from soybean oil, palm oil, rapeseed oil, corn oil, or coconut oil.

8. The formulation of claim 3 wherein said herbicidally active compound comprises atrazine, 2,4-dichlorophenoxyacetic acid (2,4-D), dicamba, glufosinate, paraquat, or a combination thereof.

9. The formulation of claim 1 wherein the at least one alkoxylated monoglyceride, at least one alkoxylated diglyceride, or a mixture thereof comprises mono and diglycerides corresponding to the formulae:

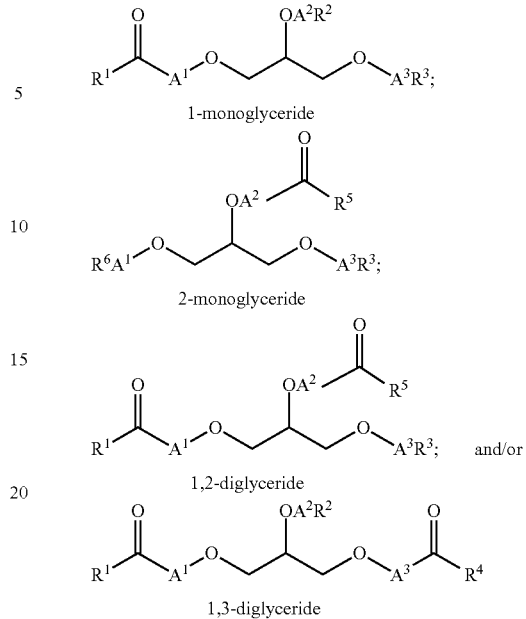

1-monoglyceride 2-monoglyceride 1,2-diglyceride and/or 1,3-diglyceride wherein each of $R^1$, $R^4$ and $R^5$ is independently selected from $C_8$ to $C_{22}$ linear or branched, saturated or unsaturated aliphatic groups, or a group of the formula

where (i) $R^{10}$ is bonded to the carbon of the acyl group (ii) each $R^{10}$ is selected from a $C_8$-$C_{22}$ linear or branched, saturated or unsaturated aliphatic group (iii) each A is the same or different and is selected from $C_1$ to $C_4$ linear or branched alkyl groups, with w from 1 to 100 and (iv) each $R^{11}$ is selected from hydrogen and a $C_8$-$C_{22}$ linear or branched, saturated or unsaturated aliphatic group; each of $R^2$, $R^3$, and $R^6$ is independently selected from H and a lower alkyl, lower alkenyl, or aryl group; and each of $A^1$, $A^2$ and $A^3$ is independently either a carbon to oxygen bond or an alkylene oxide group oriented to have a terminal O bonded to a C and a terminal C bonded to an O and containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, each of said alkoxylated mono and diglycerides contains a total of from 5 to 200 alkylene oxide units.

10. The formulation of claim 9 wherein w is from 1 to 75.

11. The formulation of claim 1 wherein the at least one alkoxylated monoglyceride, at least one alkoxylated diglyceride, or a mixture thereof comprises mono and diglycerides corresponding to the formulae:

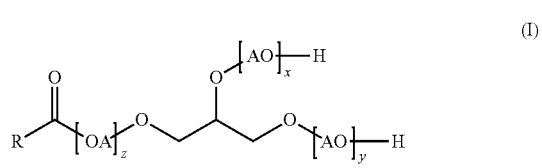

(I)

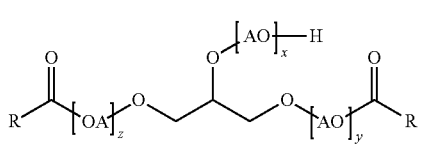
(II)

wherein each R group is independently selected from a $C_8$-$C_{22}$ linear or branched, saturated or unsaturated aliphatic group; each A is independently selected from a $C_1$ to $C_4$ linear or branched alkyl group; each of x, y and z is independently selected from an integer of from 0 to 200, with the proviso that x+y+z=5 to 2.

12. The formulation of claim 11 wherein one or more A of Formula I and/or Formula II is a $C_2$ ethyl group.

13. The formulation of claim 11 wherein each R group is independently selected from $C_{12}$-$C_{18}$ linear or branched, saturated or unsaturated alkyl group and each A group is ethylene.

14. The formulation of claim 11 wherein each R group is independently derived from soybean oil, palm oil, rapeseed oil, corn oil, or coconut oil.

15. The formulation of claim 1 wherein the at least one alkoxylated monoglyceride, at least one alkoxylated diglyceride, or a mixture thereof comprises mono and diglycerides corresponding to the formulae:

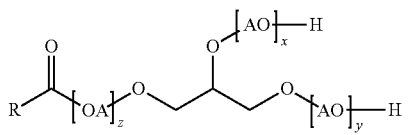
(I)

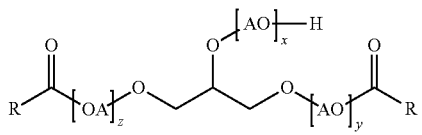
(II)

wherein each R group is independently selected from a $C_8$-$C_{22}$ linear or branched, saturated or unsaturated aliphatic group, or a group of the formula $R^{10}$—$[OA^1]v$-$R^{11}$, where
(i) $R^{10}$ is bonded to the carbon of the acyl group (ii) each $R^{10}$ is selected from a $C_8$-$C_{22}$ linear or branched, saturated or unsaturated aliphatic group (iii) each $A^1$ is the same or different and is selected from $C_1$ to $C_4$ linear or branched alkyl groups, with v from 1 to 100 and (iv) each $R^{11}$ is selected from hydrogen and a $C_8$-$C_{22}$ linear or branched, saturated or unsaturated aliphatic group; each A is independently selected from a $C_1$ to $C_4$ linear or branched alkyl group; each of x, y and z is independently selected from an integer of from 0 to 200, with the proviso that x+y+z=5 to 2.

16. The formulation of claim 15 wherein v is from 1 to 75.

17. The formulation of claim 1 comprising a mixture of ethoxylated mono- and diglycerides having a monoglyceride to diglyceride ratio of greater than about 50:50 (wt. ratio).

18. The formulation of claim 1 having a viscosity of not greater than about 800 centipoise (cPs) at 10° C. and at 45/s shear rate.

19. The formulation of claim 1 having a density of at least about 1.050 grams/liter.

20. The formulation of claim 1 wherein the at least one herbicidally active compound is glyphosate or a salt thereof and the formulation has a glyphosate content of at least about 180 g a.e./l.

21. The formulation of claim 1 wherein the at least one herbicidally active compound is glyphosate or a salt thereof and wherein the weight ratio of glyphosate (a.e.) to the sum of alkoxylated mono and diglyceride surfactant is between about 1:1 and about 30:1.

22. The formulation of claim 1 wherein the at least one herbicidally active compound is glyphosate or a salt thereof and wherein the formulation has a concentration of glyphosate in the range of from about 360 to about 600 g a.e./l, and the weight ratio of glyphosate (wt % a.e.) to the alkoxylated glyceride surfactant is between about 2:1 and about 25:1.

23. The formulation of claim 1 wherein said formulation comprises at least one co-herbicide selected from the group consisting of acifluorfen, acrolein, amitrole, asulam, benazolin, bentazon, bialaphos, bromacil, bromoxynil, chloramben, chloroacetic acid, clopyralid, 2,4-dichlorophenoxyacetic acid (2,4-D), 4-(2,4-dichlorophenoxy)butanoic acid (2,4-DB), dalapon, dicamba, dichlorprop, difenzoquat, diquat, endothall, fenac, fenoxaprop, flamprop, flumiclorac, fluoroglycofen, flupropanate, fomesafen, fosamine, glufosinate, imazameth, imazamethabenz, imazamox, imazapic, imazapyr, imazaquin, imazethapyr, ioxynil, 4-chloro-2-methylphenoxyacetic acid (MCPA), 4-(4-chloro-2-methyl-phenoxy)butanoic acid (MCPB), mecoprop, methylarsonic acid, naptalam, nonanoic acid, paraquat, picloram, quinclorac, sulfamic acid, 2,3,6-trichlorobenzoic acid (2,3,6-TBA), trichloroacetate (TCA), triclopyr, acetochlor, aclonifen, alachlor, ametryn, anilofos, atrazine, azafenidin, benfluralin, benfuresate, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlornitrofen, chlorotoluron, chlorpropham, chlorthal-dimethyl, chlorthiamid, cinmethylin, clethodim, clodinafop-propargyl, clomazone, clomeprop, cloransulam-methyl, cyanazine, cycloate, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, ethyl N,N-dipropylcarbamothioate (EPTC), esprocarb, ethalfluralin, ethofumesate, etobenzanid, fenoxaprop-ethyl, fenuron, flamprop-methyl, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, haloxyfop-methyl, hexazinone, imazamox, indanofan, isoproturon, isouron, isoxaben, isoxaflutole, isoxapyrifop, lactofen, lenacil, linuron, mefenacet, mesotrione, metamitron, metazachlor, methabenzthiazuron, methyldymron, metobenzuron, metobromuron, metolachlor, metosulam, metoxuron, metribuzin, molinate, monolinuron, naproanilide, napropamide, naptalam, neburon, norflurazon, orbencarb, oryzalin, oxadiargyl, oxadiazon, oxyfluorfen, pebulate, pendimethalin, pentanochlor, pentoxazone, phenmedipham, piperophos, pretilachlor, prodiamine, prometon, prometryn, propachlor, propanil, propaquizafop, propazine, propham, propisochlor, propyzamide, prosulfocarb, pyraflufen-ethyl, pyrazolynate, pyrazoxyfen, pyributicarb, pyridate, pyriminobac-methyl, quinclorac, quinmerac, quizalofop-ethyl, sethoxydim, siduron, simazine, simetryn, sulcotrione, sulfentrazone, tebutam, tebuthiuron, terbacil, terbumeton, terbuthylazine, terbutryn, thenylchlor, thiazopyr, thiobencarb, tiocarbazil, tralkoxydim, triallate, trietazine, trifluralin, triflusulfuron, vernolate, and salts and combinations thereof.

24. The formulation of claim 23 wherein the at least one herbicidally active compound is glyphosate or a salt thereof and the weight ratio of glyphosate (a.e.) to co-herbicide is from about 0.5 to about 4.0.

25. The formulation of claim 1 having a pH greater than about 4.

26. The formulation of claim 1 wherein the alkoxylated monoglyceride and alkoxylated diglyceride are produced by a trans esterification process which reacts glycerine with triglycerides or fatty acids followed by alkoxylation.

27. The formulation of claim 2 wherein the alkoxylated monoglyceride and alkoxylated diglyceride are produced by a trans esterification process which reacts glycerine with triglycerides or fatty acids followed by alkoxylation.

28. A solid herbicidal formulation comprising at least one herbicidally active compound and an herbicidally enhancing amount of a surfactant comprising at least one alkoxylated monoglyceride, at least one alkoxylated diglyceride, or a combination thereof, provided the composition does not contain a sulfonylurea compound, wherein the alkoxylated glycerides are mono and diglycerides corresponding to the formulae:

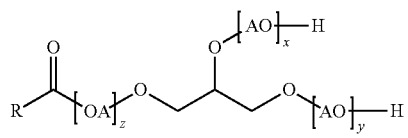
(I)

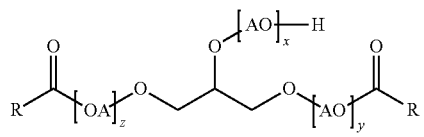
(II)

wherein each R group is independently selected from a $C_8$-$C_{22}$ linear or branched, saturated or unsaturated aliphatic group; each A is independently selected from a $C_1$ to $C_4$ linear or branched alkyl group; each of x, y and z is independently selected from an integer of from 0 to 200, with the proviso that x+y+z=5 to 200, the formulation characterized by one or more of the following:
(i) a mixture of ethoxylated mono- and diglycerides having a mono to di ratio of greater than about 50:50 (wt. ratio); and/or
(ii) a glyphosate content of at least about 180 g a.e./l; and/or
(iii) a weight ratio of glyphosate (a.e.) to the sum of alkoxylated mono and diglyceride surfactant of between about 1:1 and about 30:1; and/or
(iv) a concentration of glyphosate in the range of from about 360 to about 600 g a.e./l, and the weight ratio of glyphosate (wt % a.e.) to the alkoxylated glyceride surfactant is between about 2:1 and about 25:1.

29. A solid herbicidal formulation comprising at least one herbicidally active compound and an herbicidally enhancing amount of a surfactant comprising at least one alkoxylated monoglyceride, at least one alkoxylated diglyceride, or a combination thereof, provided the composition does not contain a sulfonylurea compound, wherein the alkoxylated glycerides are mono and diglycerides corresponding to the formulae:

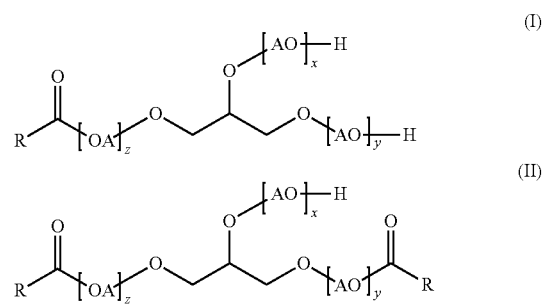

wherein each R group is independently selected from a $C_8$-$C_{22}$ linear or branched, saturated or unsaturated aliphatic group, or a group of the formula $$R^{10}-[OA^1]v-R^{11},$$ 

where
(i) $R^{10}$ is bonded to the carbon of the acyl group (ii) each $R^{10}$ is selected from a $C_8$-$C_{22}$ linear or branched, saturated or unsaturated aliphatic group (iii) each $A^1$ is the same or different and is selected from $C_1$ to $C_4$ linear or branched alkyl groups, with v from 1 to 100 and (iv) each $R^{11}$ is selected from hydrogen and a $C_8$-$C_{22}$ linear or branched, saturated or unsaturated aliphatic group; each A is independently selected from a $C_1$ to $C_4$ linear or branched alkyl group; each of x, y and z is independently selected from an integer of from 0 to 200, with the proviso that x+y+z=5 to 200, the formulation characterized by one or more of the following:
(i) a mixture of ethoxylated mono- and diglycerides having a mono to di ratio of greater than about 50:50 (wt. ratio); and/or
(ii) a glyphosate content of at least about 180 g a.e./l; and/or
(iii) a weight ratio of glyphosate (a.e.) to the sum of alkoxylated mono and diglyceride surfactant of between about 1:1 and about 30:1; and/or
(iv) a concentration of glyphosate in the range of from about 360 to about 600 g a.e./l, and the weight ratio of glyphosate (wt % a.e.) to the alkoxylated glyceride surfactant is between about 2:1 and about 25:1.

30. A solid herbicidal formulation comprising at least one herbicidally active compound and an herbicidally enhancing amount of a surfactant comprising at least one alkoxylated monoglyceride, at least one alkoxylated diglyceride, or a combination thereof, provided the composition does not contain a sulfonylurea compound, wherein the alkoxylated glycerides are mono and diglycerides corresponding to the formulae:

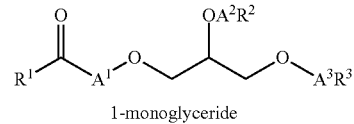

1-monoglyceride

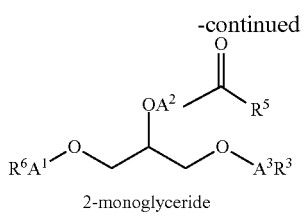

2-monoglyceride

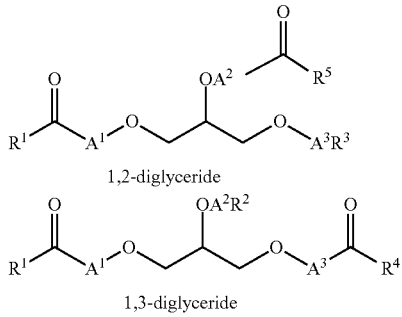

1,2-diglyceride 1,3-diglyceride wherein each of $R^1$, $R^4$ and $R^5$ is independently selected from $C_8$ to $C_{22}$ linear or branched, saturated or unsaturated aliphatic groups; each of $R^2$, $R^3$, and $R^6$ is independently selected from H and a lower alkyl, lower alkenyl, or aryl group; and each of $A^1$, $A^2$ and $A^3$ is independently either a carbon to oxygen bond or an alkylene oxide group oriented to have a terminal O bonded to a C and a terminal C bonded to an O and containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, each of said alkoxylated mono and diglycerides contains a total of from 5 to 200 alkylene oxide units, the formulation characterized by one or more of the following:
(i) a mixture of ethoxylated mono- and diglycerides having a mono to di ratio of greater than about 50:50 (wt. ratio); and/or
(ii) a glyphosate content of at least about 180 g a.e./l; and/or
(iii) a weight ratio of glyphosate (a.e.) to the sum of alkoxylated mono and diglyceride surfactant of between about 1:1 and about 30:1; and/or
(iv) a concentration of glyphosate in the range of from about 360 to about 600 g a.e./l, and the weight ratio of glyphosate (wt % a.e.) to the alkoxylated glyceride surfactant is between about 2:1 and about 25:1.

31. A solid herbicidal formulation comprising at least one herbicidally active compound and an herbicidally enhancing amount of a surfactant comprising at least one alkoxylated monoglyceride, at least one alkoxylated diglyceride, or a combination thereof, provided the composition does not contain a sulfonylurea compound, wherein the alkoxylated glycerides are mono and diglycerides corresponding to the formulae:

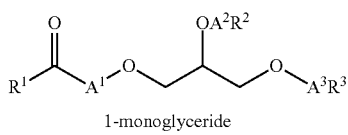

1-monoglyceride

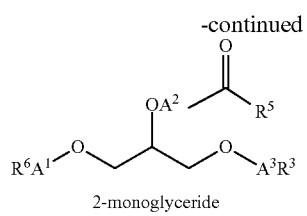

2-monoglyceride

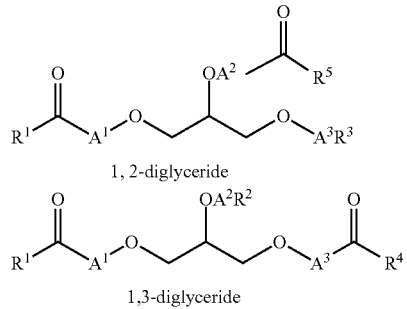

1, 2-diglyceride 1,3-diglyceride wherein each of $R^1$, $R^4$ and $R^5$ is independently selected from $C_8$ to $C_{22}$ linear or branched, saturated or unsaturated aliphatic groups or a group of the formula $R^{10}$—[OA]$w$-$R^{11}$, where
(i) $R^{10}$ is bonded to the carbon of the acyl group (ii) each $R^{10}$ is selected from a $C_8$-$C_{22}$ linear or branched, saturated or unsaturated aliphatic group (iii) each A is the same or different and is selected from $C_1$ to $C_4$ linear or branched alkyl groups, with w from 1 to 100 and (iv) each $R^{11}$ is selected from hydrogen and a $C_8$-$C_{22}$ linear or branched, saturated or unsaturated aliphatic group; each of $R^2$, $R^3$, and $R^6$ is independently selected from H and a lower alkyl, lower alkenyl, or aryl group; and each of $A^1$, $A^2$ and $A^3$ is independently either a carbon to oxygen bond or an alkylene oxide group oriented to have a terminal O bonded to a C and a terminal C bonded to an O and containing between 0 and 200 alkylene oxide units, each alkylene oxide unit being independently selected from the group consisting of —[OCH$_2$]—, —[OC$_2$H$_4$]—, —[OC$_3$H$_6$]— and —[OC$_4$H$_8$]—, each of said alkoxylated mono and diglycerides contains a total of from 5 to 200 alkylene oxide units, the formulation characterized by one or more of the following:
(i) a mixture of ethoxylated mono- and diglycerides having a mono to di ratio of greater than about 50:50 (wt. ratio); and/or
(ii) a glyphosate content of at least about 180 g a.e./l; and/or
(iii) a weight ratio of glyphosate (a.e.) to the sum of alkoxylated mono and diglyceride surfactant of between about 1:1 and about 30:1; and/or
(iv) a concentration of glyphosate in the range of from about 360 to about 600 g a.e./l, and the weight ratio of glyphosate (wt % a.e.) to the alkoxylated glyceride surfactant is between about 2:1 and about 25:1.

32. A method of controlling unwanted vegetation, said method comprising applying to said unwanted vegetation an effective amount of the herbicidal formulation of claim 2.

* * * * *